US007632980B1

(12) United States Patent
Chen et al.

(10) Patent No.: US 7,632,980 B1
(45) Date of Patent: *Dec. 15, 2009

(54) MODIFIED NUCLEIC ACID SEQUENCES AND METHODS FOR INCREASING MRNA LEVELS AND PROTEIN EXPRESSION IN CELL SYSTEMS

(75) Inventors: Li How Chen, Acton, MA (US); Harry Meade, Newton, MA (US)

(73) Assignee: GTC Biotherapeutics, Inc., Framingham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/175,683

(22) Filed: Oct. 20, 1998

Related U.S. Application Data

(60) Provisional application No. 60/062,592, filed on Oct. 20, 1997, provisional application No. 60/085,649, filed on May 15, 1998.

(51) Int. Cl.
*C12P 21/00* (2006.01)
*A01K 67/00* (2006.01)

(52) U.S. Cl. .................. 800/7; 800/13; 530/350; 536/23.7; 536/24.1

(58) Field of Classification Search .............. 530/350; 435/69.1, 252.3, 320.1, 325; 800/300, 8, 800/14, 13, 7; 536/23.1, 23.7, 23.72, 24.1
See application file for complete search history.

(56) References Cited

U.S. PATENT DOCUMENTS

| | | | | |
|---|---|---|---|---|
| 4,873,316 A | * | 10/1989 | Meade et al. ............... | 800/7 |
| 5,194,587 A | | 3/1993 | Knapp et al. | |
| 5,225,534 A | | 7/1993 | Certa | |
| 5,231,168 A | * | 7/1993 | Dziegiel et al. ............. | 530/350 |
| 5,304,489 A | * | 4/1994 | Rosen ..................... | 435/320.1 |
| 5,395,614 A | | 3/1995 | Knapp et al. | |
| 5,530,177 A | * | 6/1996 | Bleck et al. ................ | 800/7 |
| 5,543,323 A | | 8/1996 | Ridley et al. | |
| 5,643,578 A | * | 7/1997 | Robinson et al. .......... | 424/210.1 |
| 5,646,247 A | | 7/1997 | Barnwell et al. | |
| 5,736,131 A | * | 4/1998 | Bosch et al. ............... | 800/300 |
| 5,795,737 A | * | 8/1998 | Seed et al. ................. | 435/69.1 |
| 5,856,178 A | * | 1/1999 | White et al. ............... | 435/320.1 |
| 6,114,148 A | | 9/2000 | Seed et al. | |
| 6,130,062 A | | 10/2000 | Milland et al. | |
| 6,593,463 B1 | | 7/2003 | Chen et al. | |
| 7,354,594 B2 | * | 4/2008 | Chen et al. ................ | 424/268.1 |
| 2002/0144299 A1 | | 10/2002 | Chen et al. | |
| 2005/0071890 A1 | | 3/2005 | Chen et al. | |
| 2005/0235371 A1 | | 10/2005 | Chen et al. | |

FOREIGN PATENT DOCUMENTS

| | | |
|---|---|---|
| AU | 1997 48649 B2 | 4/1998 |
| AU | 727864 | 4/1998 |
| EP | 0264166 | 4/1988 |
| EP | 0359472 | 3/1990 |
| EP | 0741515 | 6/1995 |
| EP | 0 682 115 A | 11/1995 |
| EP | 0923308 | 11/1997 |
| WO | WO 91 08216 A | 6/1991 |
| WO | WO-91/18922 | 12/1991 |
| WO | WO 94/05796 | 3/1994 |
| WO | WO-94/28930 | 12/1994 |
| WO | WO 95/17085 | 6/1995 |
| WO | WO 96/03051 | 2/1996 |
| WO | WO 97/26911 | 7/1997 |
| WO | WO 97/30158 | 8/1997 |
| WO | WO/ 97/30159 * 8/1997 | ................ 435/69.1 |
| WO | WO 97/30159 | 8/1997 |
| WO | WO 97 31115 A | 8/1997 |
| WO | WO 98 14583 | 4/1998 |
| WO | WO-99/20766 | 4/1999 |
| WO | WO-99/20774 | 4/1999 |

OTHER PUBLICATIONS

Product pd(N)6 in the 1995 Pharmacia Biotech catalogue, p. 277, 1995.*
Holder et al Nature 317(6034): 270-273, See entire document, especially abstract, and Fig. 2, p. 272, Sep. 1985.*
Akashi et al Blood 83(11): 3182-3187, See entire document, especially abstract, and Fig. 1, Jun. 1994.*
Wang et al J. Biol. Chem. 264: 21116-21121, See entire document, especially Fig. 2, col. 1, p. 21118, see particularly glycine codons at positions—11 and 18, Dec. 1989.*
Liebhaber, Nucleic Acids Symp Ser, 1997; (36): 29-32.*
Lukashov et.al., 1996; Accession L48364.*
Simons et al (Bio/Technology 6: 179-183, 1988).*
Gordon et al.; Genetic Transformation of Mouse Enbruos by Microinjection of Purified DNA; (1980); *Proc. Natl. Acad. Sci.*; 77: pp. 7380-7384.
Gordon et al.; Integration and Stable Germ Line Transmission of Genes Injected into Mouse Pronuclei; (1981); *Science*; 214: pp. 1244-1246.
Brinster et al.; Factors Affecting the Efficiency of Introducing Foreing DNA into Mice by Microinjecting Eggs; (1985); *Proc. Natl. Acad. Sci.*; 82: pp. 4438-4442.
Palmiter et al.; Transgenic Mice; (1985); *Cell*; 41: pp. 343-345.

(Continued)

Primary Examiner—Richard Schnizer
(74) Attorney, Agent, or Firm—Wolf, Greenfield & Sacks, P.C.

(57) ABSTRACT

The invention provides modified recombinant nucleic acid sequences (preferably DNA) and methods for increasing the mRNA levels and protein expression of proteins which are known to be, or are likely to be, difficult to express in cell culture systems, mammalian cell culture systems, or in transgenic animals. The preferred "difficult" protein candidates for expression using the recombinant techniques of the invention are those proteins derived from heterologous cells preferably those of lower organisms such as parasites, bacteria, and virus, having DNA coding sequences comprising high overall AT content or AT rich regions and/or mRNA instability motifs and/or rare codons relative to the recombinant expression system to be used.

8 Claims, 15 Drawing Sheets

OTHER PUBLICATIONS

Wall et al.; Development of Porcine Ova That Were Centrifuged to Permit Visualization of Pronuclei and Nuclei[1]; (1985); *Biol. Reprod.*; 32: pp. 645-651.

Shaw et al.; A Conserved AU Sequence from the 3' Untranslated Region of GM-CSF mRNA Mediates Selective mRNA Degradation; (1986); *Cell*; 46: pp. 659-667.

Chang et al.; Generalized Immunological Recognition of the Major Merozoite Surface Antigen (gp195) of *Plasmodium falciparum*; (1989); *Proc. Natl. Acad. Sci.*; 86: pp. 6343-6347.

Vilotte et al.; Efficient Tissue-Specific Expression of Bovine α lactalbumin in Transgenic Mice; (1989); *Eur. J. Biochem.*; 186 pp. 43-48.

Buhler et al.; Rabbit β-Casein Promotor Directs Secretion of Human Interleukin-2 into the Milk of Transgenic Rabbits; (1990); *Bio/Technology*; 8: pp. 140-143.

Ebert et al.; Transgenic Production of A Variant of Human Tissue-Type Plasminogen Activator in Goat Milk Generation of Transgenic Goats . . . ; (1991);*Bio/Technology*; 9: pp. 835-838.

Krimenfort et al.; Generation of Transgenic Dairy Cattle Using 'In Vitro' Embryo Production; (1991) *Bio/Technology*; 9: pp. 844-847.

Wright et al.; High Level Expression of Active Human Alpha-1-Antitrypsin in the Milk of Transgenic Sheep; (1991); *Bio/Technology*; 9: 830-834.

Chang et al.; A Carboxyl-Terminal Fragment of *Plasmodium falciparum* gp195 Expression by a Recombinant Baculovirus Induces Antibodies that . . . ; (1992); *J. Immunol*; 149: pp. 548-555.

Soulier et al.; Expression Analysis of Ruminant α-Lactalbumin in Transgenic Mice: Developmental Regulation and General Location of Important *Cis*-Regulatory . . . ; (1992); *FEBS Letters*: 297(1-2): pp. 13-18.

Wall et al.; Making Transgenic Livestock: Genetic Engineering on a Large Scale: (1992); *J. Cell. Biochem.*; 49: pp. 113-120.

Diggs et al.; The Major Merozoite Surface Protein as a Malaria Vaccine Target; (1993); *Parasitology Today*; 9(8): pp. 300-302.

Campbell et al.; Sheep Coloned by Nuclear Transfer from a Cultured Cell Line; (1996); *Nature*; 380: pp. 64-66.

Chang et al.; A Recombinant Baculovirus 42-Kilodalton C-Terminal Fragment of *Plasmodium falciparum* Merozoite Surface Protein 1 Protects *Aotus* Monkeys . . . ; (1996); *Infection & Immunity*; 64(1): pp. 253-262.

Hochi et al.; Secretion of Bovine α-Lactalbumin into the Milk of Transgenic Rats, (1992) *Molecular Reproduction and Development* 33:160-164.

Chattergoon et al., Genetic immunization: a new era in vaccines and immune therapeutics. FASEB J. Aug. 1997;11(10);753-63.

Dame et al., Current status of the *Plasmodium falciparum* genome project. Mol Biochem Parasitol. Jul. 1996;79(1):1-12.

D'Orso et al., TcUBP-1, a developmentally regulated U-rich RNA-binding protein involved in selective mRNA destabilization in trypanosomes. J Biol Chem. Sep. 14, 2001;276(37):34801-9 Epub Jul. 2, 2001.

Gardner et al., DNA vaccines against malaria: immunogenicity and protection in a rodent model. J Pharm Sci. Dec. 1996;85(12):1294-300.

Graves et al., Comparison of the cost-effectiveness of vaccines and insecticide impregnation of mosquito nets for the prevention of malaria. Ann Trop Med Parasitol. Jun. 1998;92(4):399-410.

Graves et al., Vaccines for preventing malaria. Cochrane Database Syst Rev. 2003;(1):CD000129.

Gutierrez et al., Expression of a bovine kappa-CN cDNA in the mammary gland of transgenic mice utilizing a genomic milk protein gene as an expression cassette, Transgenic Res. Jul. 1996;5(4):271-9.

Jenkins et al., Evolution of base composiiton and codon usage bias in the genus Flavivirus. J Mol Evol. Apr. 2001;52(4):383-90.

Jongwutiwes et al., Sequence conservation in the C-terminal part of the precursor to the major merozoite surface proteins (MSP1) of *Plasmodium falciparum* from field isolates. Mol Biochem Parasitol. May 1993;59(1):95-100.

Kalinna et al., DNA vaccines for parasitic infections. Immunol Cell Biol. Aug. 1997;75(4):370-5.

Ledley et al., Clinical considerations in the design of protocols for somatic gene therapy. Hum Gene Ther. 1991 Spring;2(1):77-83.

Martin et al., Total synthesis and expression in *Escherichia coli* of a gene encoding human tropoelastin. Gene. Mar. 10, 1995;154(2):159-66.

McDonnell et al., DNA vaccines. N Engl J Med. Jan. 4, 1996;334(1):42-5.

Nuijens et al., Characterization of recombinant human lactoferrin secreted in milk of transgenic mice. J Biol Chem. Mar. 28, 1997;272(13):8802-7.

Orkin et al., Report and recommendations of panel to assess NIH investment in Gene Therapy Res. 1995.

Perlak et al., Modification of the coding sequence enhances plant expression of insect control protein genes. Proc Natl Acad Sci U S A. Apr. 15, 1991;88(8):3324-8.

Prapunwattana et al., Chemical synthesis of the *Plasmodium falciparum* dihydrofolate reductase-thymidylate synthase gene. Mol Biochem Parasitol. Dec. 2, 1996;83(1):93-106.

Senior et al., DNA vaccine show promise for malaria. Mol Med Today. Jan. 1999;5(1):2-3.

Shani et al., Expression of human serum albumin in the milk of transgenic mice. Transgenic Res. Sep. 1992;1(5):195-208.

Urdea et al., Chemical synthesis of a gene for human epidermal growth factor urogastrone and its expression in yeast. Proc. Natl Acad Sci U S A. Dec. 1983;80(24):7461-5.

Velander et al., High-level expression of a heterologous protein in the milk of transgenic swine using the cDNA encoding human protein C. Proc Natl Acad Sci U S A. Dec. 15, 1992;89(24):12003-7.

Weber et al., Analysis of sequences from the extremely A + T-rich genome of *Plasmodium falciparum*. Gene. 1987;52(1):103-9.

Wesseling et al., Nucleotide sequence and deduced amino acid sequence of a *Plasmodium falciparum* actin gene. Mol Biochem Parasitol. Jan. 15, 1988;27(2-3):313-20.

Wu et al., Transfection of *Plasmodium falciparum* within human red blood cells. Proc Natl Acad Sci U S A . Feb. 14, 1995;92(4):973-7.

Zientz et al., Genome interdependence in insect-bacterium symbioses. Genome Biol. 2001;2(12):REVIEWS1032. Epub Nov. 22, 2001.

Zinkernagel et al., Immunity to viruses. Chapter 34: Fundamental Immunology. 3rd Edition, Raven Press. 1993.

Amendment filed in Response on Apr. 18, 2007 for U.S. Appl. No. 10/949,975 (Li-How Chen, filed Sep. 24, 2004).

Preliminary Amendment filed on Sep. 23, 2002 for U.S. Appl. No. 09/175,684 (Li-How Chen, filed Oct. 20, 1998).

Preliminary Amendment filed on Sep. 18, 2002 for U.S. Appl. No. 09/175,684 (Li-How Chen, filed Oct. 20, 1998).

Amendment filed in Response with Declaration on Sep. 10, 2004 for U.S. Appl. No. 10/082,018 (Li-How Chen, filed Feb. 20, 2002) (Declaration only).

Office Communication with Interview Summary mailed Aug. 9, 2005 for U.S. Appl. No. 10/082,018 (Li-How Chen, filed Feb. 20, 2002).

Carver et al., Expression of Human Alpha 1 Antitrypsin In Transgenic Sheep. Cytotechnology. 1992;9(1-3):77-84.

Eskridge et al., The NH2 terminus of preproinsulin directs the translocation and glycosylation of a bacterial cytoplasmic protein by mammalian microsomal membranes. J. Cell. Biol. 103(6):2263-2272 (1996).

Hirabayashi et al., Transgene Expression In Mammary Glands of Newborn Rats. Mol. Reprod. Dev. Feb. 1996;43(2):145-9.

Holder et al., The precursor to major merozoite surface antigens: structure and role in immunity. Prog. Allergy. 41:72-97 (1988).

Kotula et al., Evaluation of foreign gene codon optimization in yeast: expression of a mouse IG kappa chain. Biotechnology 9(10):1386-1389 (1991).

Marshall et al., Naturally occurring splicing variants of the hMSH2 gene containing nonsense codons identify possible mRNA instability motifs within the gene coding region, Biochem Biophys Acta. Jul. 31, 1996;1308(1):88-92.

Peterson et al., Variation in the precursor to the major merozoite surface antigens of *Plasmodium falciparum*. Mol. Biochem. Parisitol 27:291-302 (1988).

Prunkard et al., High-Level Expression o f Recombinant Human Fibrinogen in the Milk of Transgenic Mice. Nat. Biotechnol. Jul. 1996;14(7):867-71.

Reeck, G R et al., "Homology" in Proteins and Nucleic Acids: A Terminology Muddle and a Way out of it., 1987, Cell 50:667.

Van Cott et al., Affinity Purification of Biologically Active and Inactive Forms of Recombinant Human Protein C Produced In Porcine Mammary Gland. J. Mol. Recognit. Sep.-Dec. 1996; 9(5-6):407-14.

Wang et al., Molecular cloning, gene organization and expression of rainbow trout (*Oncorhynchus mykiss*) inducible nitric oxide synthase (iNOS) gene. Biochem J. Sep. 15, 2001;358(Pt 3):747-55.

Ziomek Minimization of Viral Contamination In Human Pharmaceuticals Produced in the Milk of Transgenic Goats. Dev. Biol. Stand. 1996;88:265-8.

Office Communication mailed Oct. 18, 2006 for U.S. Appl. No. 10/949,975 (Li-How Chen et al., filed Sep. 24, 2004).

Amendment filed in Response on Jun. 8, 2007 for U.S. Appl. No. 10/949,975 (Li-How Chen et al., filed Sep. 24, 2004).

Office Communication mailed Jul. 26, 2007 for U.S. Appl. No. 10/949,975 (Li-How Chen et al., filed Sep. 24, 2004).

Office Communication mailed Jun. 20, 2000 for U.S. Appl. No. 09/175,684 (Li-How Chen et al., filed Oct. 20, 1998).

Amendment filed in Response on Dec. 20, 2000 for U.S. Appl. No. 09/175,684 (Li-How Chen et al., filed Oct. 20, 1998).

Office Communication mailed Mar. 14, 2001 for U.S. Appl. No. 09/175,684 (Li-How Chen et al., filed Oct. 20, 1998).

Amendment filed in Response on Aug. 14, 2001 for U.S. Appl. No. 09/175,684 (Li-How Chen et al., filed Oct. 20, 1998).

Notice of Allowance with Interview and Examiner's Amendment mailed Nov. 19, 2001 for U.S. Appl. No. 09/175,684 (Li-How Chen et al., filed Oct. 20, 1998).

Interview Summary mailed Jan. 23, 2002 for U.S. Appl. No. 09/175,684 (Li-How Chen et al., filed Oct. 20, 1998).

Notice of Allowance with Interview Summary and Examiner's Amendment mailed Nov. 13, 2002 for U.S. Appl. No. 09/175,684 (Li-How Chen et al., filed Oct. 20, 1998).

Office Communication mailed Mar. 10, 2004 for U.S. Appl. No. 10/082,018 (Li-How Chen, filed Feb. 20, 2002).

Amendment filed in Response on Sep. 10, 2004 for U.S. Appl. No. 10/082,018 (Li-How Chen, filed Feb. 20, 2002).

Office Communication mailed Nov. 29, 2004 for U.S. Appl. No. 10/082,018 (Li-How Chen, filed Feb. 20, 2002).

Amendment filed in Response on May 27, 2005 for U.S. Appl. No. 10/082,018 (Li-How Chen, filed Feb. 20, 2002).

Office Communication mailed Aug. 9, 2005 for U.S. Appl. No. 10/082,018 (Li-How Chen, filed Feb. 20, 2002).

Amendment filed in Response on Jan. 30, 2006 for U.S. Appl. No. 10/082,018 (Li-How Chen, filed Feb. 20, 2002).

Notice of Allowability and Examiner's Amendment mailed Apr. 25, 2006 for U.S. Appl. No. 10/082,018 (Li-How Chen, filed Feb. 20, 2002).

Notice of Allowability with Examiner's Amendment and Interview Summary mailed Sep. 17, 2007 for U.S. Appl. No. 10/082,018 (Li-How Chen, filed Feb. 20, 2002).

Office Communication mailed Nov. 18, 2005 for U.S. Appl. No. 11/140,676 (Li-How Chen et al., filed May 27, 2005).

Amendment filed in Response on Nov. 29, 2005 for U.S. Appl. No. 11/140,676 (Li-How Chen et al., filed May 27, 2005).

Office Communication mailed May. 3, 2007 for U.S. Appl. No. 11/140,676 (Li-How Chen et al., filed May 27, 2005).

Amendment filed in Response on Aug. 3, 2007 for U.S. Appl. No. 11/140,676 (Li-How Chen et al., filed May 27, 2005).

Search Report for EP application No. 04022373.7—2406 (Chen et al., filed Sep. 21, 2004) mailed Jan. 26, 2006.

Myler, P J, Nucleotide and deduced amino acid sequence of the gp195 (MSA-1) gene from *Plasmodium falciparum* Palo Alto PLF-3/B11, 1989, Nucleic Acids Research 17:5401.

Romanos, M A et al., Expression of tetanus toxin fragment C in yeast: gene synthesis is required to eliminate fortuitous polyadenylation in AT-rich DNA. 1991 Nucleic Acids Research 19(7):1461-1467.

Notice of Allowance and Fees Due with Reasons for Allowance and Examiner-Initiated Interview Summary mailed Nov. 19, 2007 for U.S. Appl. No. 11/140,676 (Chen et al., filed May 27, 2005).

Notice of Allowance and Fees Due mailed Dec. 19, 2007 for U.S. Appl. No. 10/082,018 (Chen et al., filed Feb. 20, 2002).

Siddiqui, W A et al., Merozoite surface coat precursor protein completely protects Aotus monkeys against *Plasmodium falciparum* malaria., May, 1987, *Proc. Natl. Acad. Sci. USA*, 84:3014-3018.

Holder, A A et al., Processing of the precursor to the major merozoite surface antigens of *Plasmodium falciparum*, 1987, *Parasitology*, 94:199-208.

Hogh et al., "Antibodies to a recombinant glutamate-rich *Plasmodium Falciparum* protein: evidence for protection of individuals living in a holoendemic area of liberia," *Am. J. Trop. Med. Hyg.*, 1992, 46(3):307-13.

Kocken et al., "High-level expression of *Plasmodium vivax* apical membrane antigen 1 (AMA-1) in *Pichia pastoris*: strong immunogenicity in *Macaca mulatta* immunized with *P. vivax* AMA-1 and Adjuvant SBAS2," *Int: Imm.*, 1999, 67(1):43-9.

Theisen et al., "Antigenicity and immunogenicity of recombinant glutamate-rich protein of *Plasmodium falciparum* expressed in *Escherichia coli*," *Clin. Diag. Lab. Immunol.*, 1995, 2(1):30-4.

Theisen et al., "The glutamate-rich protein (GLURP) of *Plasmodium falciparum* is a target for antibody-dependent monocyte-mediated inhibition of parasite growth in vitro," *Inf. Imm.*, 1998, 66(1):11-7.

* cited by examiner

Fig.1

```
   1  CCAGTAACTCCTTCCGTAATTGATAACATACTTTCTAAAATTGAAAATGAATATG
   1▶ AlaValThrProSerValIleAspAsnIleLeuSerLysIleGluAsnGluTyrG
                                                  EcoNI (72)
  56  AGGTTTTATATTTAAAACCTTTAGCAGGTGTTTATAGAAGTTTAAAAAAACAATT
  19▶ luValLeuTyrLeuLysProLeuAlaGlyValTyrArgSerLeuLysLysGlnLe
 111  AGAAAATAACGTTATGACATTTAATGTTAATGTTAAGGATATTTAAATTCACGA
  37▶ uGluAsnAsnValMetThrPheAsnValAsnValLysAspIleLeuAsnSerArg
 166  TTTAATAAACGTGAAAATTTCAAAAATGTTTTAGAATCAGATTTAATTCCATATA
  56▶ PheAsnLysArgGluAsnPheLysAsnValLeuGluSerAspLeuIleProTyrL
 221  AAGATTTAACATCAAGTAATTATGTTGTCAAAGATCCATATAAATTTCTTAATAA
  74▶ ysAspLeuThrSerSerAsnTyrValValLysAspProTyrLysPheLeuAsnLy
 276  AGAAAAAGACATAAATTCTTAAGCAGTTATAATTATATTAAGGATTCAATAGAT
  92▶ sGluLysArgAspLysPheLeuSerSerTyrAsnTyrIleLysAspSerIleAsp
 331  ACGGATATAAATTTTGCAAATGATGTTCTTGGATATTATAAAATATTATCCGAAA
 111▶ ThrAspIleAsnPheAlaAsnAspValLeuGlyTyrTyrLysIleLeuSerGluL
 386  AATATAAATCAGATTTAGATTCAATTAAAAAATATATCAACGACAAACAAGGTGA
 129▶ ysTyrLysSerAspLeuAspSerIleLysLysTyrIleAsnAspLysGlnGlyGl
 441  AAATGAGAAATACCTTCCCTTTTTAAACAATATTGAGACCTTATATAAAACAGTT
 147▶ uAsnGluLysTyrLeuProPheLeuAsnAsnIleGluThrLeuTyrLysThrVal
 496  AATGATAAAATTGATTTATTTGTAATTCATTTAGAAGCAAAAGTTCTAAATTATA
 166▶ AsnAspLysIleAspLeuPheValIleHisLeuGluAlaLysValLeuAsnTyrT
 551  CATATGAGAAATCAAACGTAGAAGTTAAAATAAAAGAACTTAATTACTTAAAAAC
 184▶ hrTyrGluLysSerAsnValGluValLysIleLysGluLeuAsnTyrLeuLysTh
 606  AATTCAAGACAAATTGGCAGATTTTAAAAAAATAACAATTTCGTTGGAATTGCT
 202▶ rIleGlnAspLysLeuAlaAspPheLysLysAsnAsnAsnPheValGlyIleAla
 661  GATTTATCAACAGATTATAACCATAATAACTTATTGACAAAGTTCCTTAGTACAG
 221▶ AspLeuSerThrAspTyrAsnHisAsnAsnLeuLeuThrLysPheLeuSerThrG
 716  GTATGGTTTTTGAAAATCTTGCTAAAACCGTTTTATCTAATTTACTTGATGGAAA
 239▶ lyMetValPheGluAsnLeuAlaLysThrValLeuSerAsnLeuLeuAspGlyAs
 771  CTTGCAAGGTATGTAAACATTTCACAACACCAATGCGTAAAAAAACAATGTCCA
 257▶ nLeuGlnGlyMetLeuAsnIleSerGlnHisGlnCysValLysLysGlnCysPro
 826  CAAAATTCTGGATGTTTCAGACATTTAGATGAAAGAAGAATGTAAATGTTTAT
 276▶ GlnAsnSerGlyCysPheArgHisLeuAspGluArgGluGluCysLysCysLeuL
 881  TAAATTACAAACAAGAAGGTGATAAATGTGTTGAAAATCCAAATCCTACTTGTAA
 294▶ euAsnTyrLysGlnGluGlyAspLysCysValGluAsnProAsnProThrCysAs
 936  CGAAAATAATGGTGGATGTGATGCAGATGCCAAATGTACCGAAGAAGATTCAGGT
 312▶ nGluAsnAsnGlyGlyCysAspAlaAspAlaLysCysThrGluGluAspSerGly
 991  AGCAACGGAAGAAAATCACATGTAATGTACTAAACCTGATTCTTATCCACTTT
 331▶ SerAsnGlyLysLysIleThrCysGluCysThrLysProAspSerTyrProLeuP
                                                  PstI (1058)
1046  TCGATGGTATTTTCTGCAGTCACCACCACCACCACCACTAACT
 349▶ heAspGlyIlePheCysSerHisHisHisHisHisHis···
```

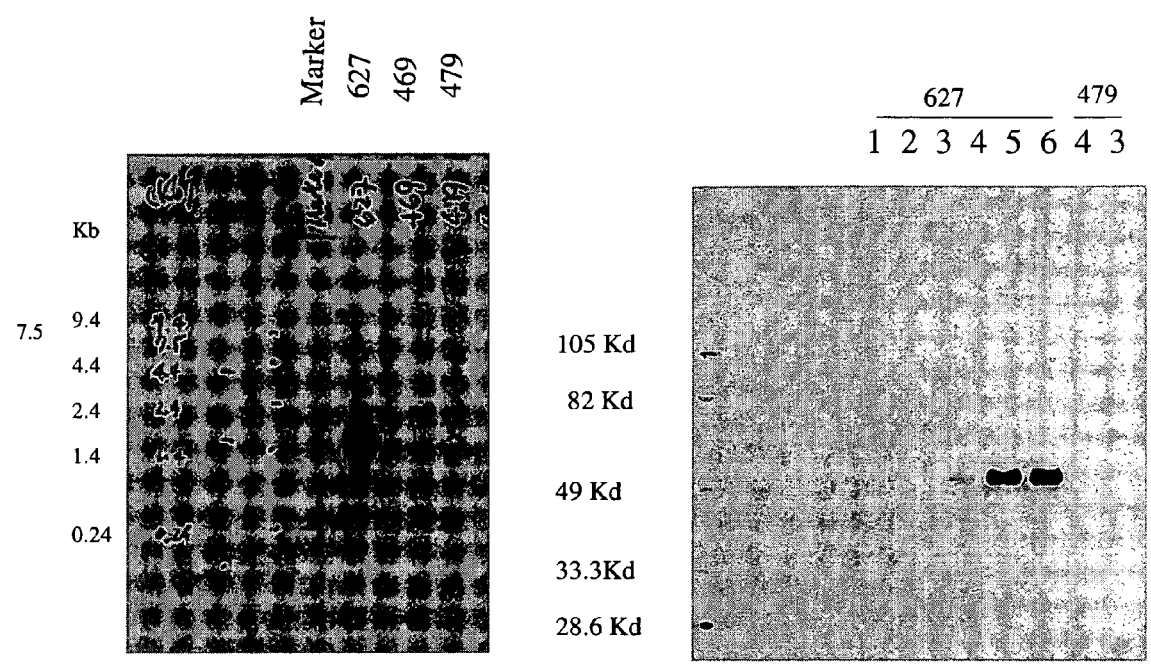
Fig. 5 Panel A            Fig. 5 Panel B

Oligos used:
Sequence ID NO. 3:

TCG ACG AGA GCC ATG AAG GTC CTC ATC CTT GCC TGT CTG GTG GCT
CTG GCC ATT GCA AGA GAG CAG GAA GAA CTC AAT GTA GTC GGT A,

Sequence ID NO. 4:

GAT CTA CCG ACT ACA TTG AGT TCT TCC TGC TCT CTT GCA ATG GCC
AGA GCC ACC AGA CAG GCA AGG ATG AGG ACC TTC ATG GCT CTC G,

Sequence ID NO. 5:

AATAGATCTGCAGTAACTCCCTTCCGTAATTG,

Sequence ID NO. 6:

AATTCTCGAGTTAGTGGTGGTGGTGGTGACTGCAGAAATACCATC

Sequence ID NO. J:

TAACTCGAGGCGAACCATGAAGGTCCCTCATCCTTGCCTGTCTGGTGGCTCTGG
CCATTGCA

FIG. 6

```
  26 CATGAAGTCCTCATAATTGCCGTCGTGGCTCTGGCACTTGCAGCCGTCACCCCGTCAATCGATAA
   1▶ M  K  V  L  I  I  A  C  L  V  A  L  A  L  A  A  V  T  P  S  V  I  D  N
  98 CATCCTGTCCAAGATCGAGAACGAGTACGAAGTCCTGTATCTGAAGCCCCTGGCAGGAGTCTACAGGAGCC
  24▶ I  L  S  K  I  E  N  E  Y  E  V  L  Y  L  K  P  L  A  G  V  Y  R  S
 169 TGAAGAAGCAGCTGGAGAACAACGTGATGACCTTCAACGTGAACGTTGAAGGATATCCTGAACAGCAGGTTCA
  48▶ L  K  K  Q  L  E  N  N  V  M  T  F  N  V  N  V  K  D  I  L  N  S  R  F
 241 ACAAGAGGGAGAACTTCAAGAACGTGCTGGAGAGCGATCTGATCCCTACAAGGATCGACCAGCAGCAACT
  72▶ N  K  R  E  N  F  K  N  V  L  E  S  D  L  I  P  Y  K  D  L  T  S  S  N
                                                     AAGAGAGATAAGTTCCTGAGCAGTTACAATTACA
 313 ACGTGGTCAAAGAT
                EcoNI (337)
  96▶ Y  V  V  K  D  P  Y  K  F  L  N  K  E  K  R  D  K  F  L  S  S  Y  N  Y
 385 TCAAGGATAGCATTGACACCGATATCAACTTCGCCAACGATGTCCTGGATACTACAAAGATCCTGTCCGAGA
 120▶ I  K  D  S  I  D  T  D  I  N  F  A  N  D  V  L  G  Y  Y  K  I  L  S  E
 457 AGTACAAGAGCGATC                                           GGA
              NdeI (621)
 144▶ K  Y  K  S  D  L  D  S  I  K  K  Y  I  N  D  K  Q  G  E  N  E  K  Y  L
 529 CCTTCCTGAACAACATCGAGACCCTGTACAAGACCGTCAACGATAAGATTGATCTGTTCGTGATCCACCTGG
 168▶ P  F  L  N  N  I  E  T  L  Y  K  T  V  N  D  K  I  D  L  F  V  I  H  L
                                          AGAGCAACGTGGAGGTCAAGATCAAGGAGCTGAATTACCTGA
 601 AGGCCAAG           CAG
                 CAG
 192▶ E  A  K  V  L  Q  Y  T  Y  E  K  S  N  V  E  V  K  I  K  E  L  N  Y  L
 673 AGACCATCCAGGATAAGCTGGCCGATTTCAAGAAGAACAACAACTTCGTCGGAATCGCCGATCTGAGACCG
                                                   BsmI (849)
 216▶ K  T  I  Q  D  K  L  A  D  F  K  K  N  N  N  F  V  G  I  A  D  L  S  T
 745 ATTACAACCACCACAACCTGCTGACCAAGTTCCTGAGCACCGGAATGGTCTTCGAAAACCTGGCCAAGACCG
 240▶ D  Y  N  H  N  N  L  L  T  K  F  L  S  T  G  M  V  F  E  N  L  A  K  T
 817 TCCTGAGCAACCTGCTGGATGGAAACCTG                CAGCAACCAGTGCTGTGAAGAAAG
 264▶ V  L  S  N  L  L  D  G  N  L  Q  G  M  L  Q  I  S  Q  H  Q  C  V  K  K
 888 CAGTGTCCCCAGAACAGCGGATGCTTCAGACACCTGGATGAGGAGTGCAAGTGCCTGCTGAACT
 288▶ Q  C  P  Q  N  S  G  C  F  R  H  L  D  E  R  E  E  C  K  C  L  L  N
 958 ACAAGCAGGAAAGGAGATAAGCTGTGTGGAAAACCCCATCTACTTGTAAACGAGAACAATGAGGATGCCAT
 311▶ Y  K  Q  E  G  D  K  C  V  E  N  P  N  P  T  C  N  E  N  N  G  G  C  D
1029 GCCGATGCCAAGTGTTACCGAGGATTCAGGAAGCACTGCCGAGTGTACCAAGCC
 335▶ A  D  A  K  C  T  E  E  D  S  G  N  G  K  K  I  T  C  E  C  T  K  P
                                                                  XhoI (1157)
1100 TGAATTCTTATCCACTGTTCGATGGTATTTTCTGCAGTCACCACCACCACCACCACTAACTCGAGGATCC
 358▶ D  S  Y  P  L  F  D  G  I  F  C  S  H  H  H  H  H  H  *  L  E  D
```

Fig. 11

| | |
|---|---|
| 1. | MW marker |
| 2. | MSP19 |
| 3. | Neg Milk |
| 4. | 39 BC718 |
| 5. | 42 BC718 |
| 6. | 49 BC718 |
| 7. | 51 BC718 |
| 8. | 84 BC718 |
| 9. | 85 BC718 |
| 10. | 106 BC670 |
| 11. | 123 BC670 |
| 12. | 148 BC670 |

MODIFIED NUCLEIC ACID SEQUENCES AND METHODS FOR INCREASING MRNA LEVELS AND PROTEIN EXPRESSION IN CELL SYSTEMS

This application claims the benefit of previously filed Provisional Application Nos. 60/062,592, filed Oct. 20, 1997 and 60/085,649, filed May 15, 1998, the contents of which are incorporated in their entirety.

BACKGROUND OF THE INVENTION

1. Field of the Invention

The invention relates to heterologous gene expression. More particularly, the invention relates to the expression of microbial or parasitic organism genes in higher eukaryote cell systems.

2. Summary of the Related Art

Recombinant production of certain heterologous gene products is often difficult in in vitro cell culture systems or in vivo recombinant production systems. For example, many researchers have found it difficult to express proteins derived from bacteria, parasites and virus in cell culture systems different from the cell from which the protein was originally derived, and particularly in mammalian cell culture systems. One example of a therapeutically important protein which has been difficult to produce by mammalian cells is the malaria merozoite surface protein (MSP-1).

Malaria is a serious heath problem in tropical countries. Resistance to existing drugs is fast developing and a vaccine is urgently needed. Of the number of antigens that get expressed during the life cycle of *P. falciparum*, MSP-1 is the most extensively studied and promises to be the most successful candidate for vaccination. Individuals exposed to *P. falciparum* develop antibodies against MSP-1, and studies have shown that there is a correlation between a naturally acquired immune response to MSP-1 and reduced malaria morbidity. In a number of studies, immunization with purified native MSP-1 or recombinant fragments of the protein has induced at least partial protection from the parasite (Diggs et al, (1993) *Parasitol. Today* 9:300-302). Thus MSP-1 is an important target for the development of a vaccine against *P. falciparum*.

MSP-1 is a 190-220 kDA glycoprotein. The C-terminal region has been the focus of recombinant production for use as a vaccine. However, a major problem in developing MSP-1 as a vaccine is the difficulty in obtaining recombinant proteins in bacterial or yeast expression systems that are equivalent in immunological potency to the affinity purified native protein (Chang et al., (1992) *J. Immunol.* 148:548-555.) and in large enough quantities to make vaccine production feasible.

Improved procedures for enhancing expression of sufficient quantities of proteins derived from parasite, bacterial and viral organisms which have previously been difficult to produce recombinantly would be advantageous. In particular, a recombinant system capable of expressing MSP-1 in sufficient quantities would be particularly advantageous.

BRIEF SUMMARY OF THE INVENTION

The present invention provides improved recombinant DNA compositions and procedures for increasing the mRNA levels and protein expression of proteins derived from heterologous cells, preferably those of lower organisms such as bacteria, virus, and parasite, which have previously been difficult to express in cell culture systems, mammalian cell culture systems, or in transgenic mammals. The preferred protein candidates for expression in an expression system in accordance with the invention are those proteins having DNA coding sequences comprising high overall AT content or AT rich regions, and/or mRNA instability motifs and/or rare codons relative to the recombinant expression systems.

In a first aspect, the invention features a modified known nucleic acid, preferably a gene from a bacterium, virus or parasite, capable of being expressed in a system, wherein the modification comprises a reduced AT content, relative to the unmodified sequence, and optionally further comprises elimination of at least one or all mRNA instability motifs present in the natural gene. In certain preferred embodiments the modification further comprises replacement of one or more codons of the natural gene with preferred codons of the cell system.

In a second aspect, the invention provides a process for preparing a modified nucleic acid of the invention comprising the steps of lowering the overall AT content of the natural gene encoding the protein, and/or eliminating at least one or all mRNA instability motifs and/or replacing one or more codons with a preferred codon of the cell system of choice, all by replacing one or more codons in the natural gene with codons recognizable to, and preferably with codons preferred by the cell system of choice and which code for the same amino acids as the replaced codon. This aspect of the invention further includes modified nucleic acids prepared according to the process of the invention.

In a third aspect, the invention also provides vectors comprising nucleic acids of the invention and promoters active in the cell line or organism of choice, and host cells transformed with nucleic acids of the invention.

In a fourth aspect, the invention provides transgenic expression vectors for the production of transgenic lactating animals comprising nucleic acids of the invention as well as transgenic non-human lactating animals whose germlines comprise a nucleic acid of the invention.

In a fifth aspect, the invention provides a transgenic expression vector for production of a transgenic lactating animal species comprising a nucleic acid of the invention, a promoter operatively coupled to the nucleic acid which directs mammary gland expression of the protein encoded by the nucleic acid into the milk of the transgenic animal.

In a sixth aspect, the invention provides a DNA vaccine comprising a modified nucleic acid according to the invention. A preferred embodiment of this aspect of the invention comprises a fragment of a modified MSP-1 gene according to the invention.

DESCRIPTION OF THE DRAWINGS

FIG. 1 depicts the cDNA sequence of MSP-$1_{42}$ modified in accordance with the invention (SEQ ID NO:1) in which 306 nucleotide positions have been replaced to lower AT content and eliminate mRNA instability motifs while maintaining the same protein amino acid sequence of MSP-$1_{42}$ (SEQ ID NO:9). The large letters indicate nucleotide substitutions.

FIG. 2 depicts the nucleotide sequence coding sequence of the "wild type" or native MSP-$1_{42}$ (SEQ ID NO:2) and predicted amino acid sequence (SEQ ID NO:10).

FIG. 3a is a codon usage table for wild type MSP-$1_{42}$ (designated "MSP wt" in the table) and the new modified MSP-$1_{42}$ gene (designated "edited MSP" in the table) and several milk protein genes (casein genes derived from goats and mouse). The numbers in each column indicate the actual number of times a specific codon appears in each of the listed genes. The new MSP-$1_{42}$ synthetic gene was derived from the mammary specific codon usage by first choosing GC rich codons for a given amino acid combined with selecting the amino acids used most frequently in the milk proteins.

FIG. 3b is a codon usage table comparing the number of times each codon appears in both the wild type MSP-1$_{42}$ (designated "MSP wt" in the table) and the new modified MSP-1$_{42}$.gene (designated "edited MSP" in the table) as is also shown in the table in FIG. 3a. The table in FIG. 3b, also compares the frequency in which each codon appears in the wild type MSP-1$_{42}$ and the new modified MSP-1$_{42}$ gene, to the frequency of appearance of each codon in both E. coli genes and human genes. Thus, if the expression system were E. coli cells, this table may be used to determine what codons are recognized by, or preferred by E. coli.

FIG. 5 panel A is a Northern analysis wherein construct GTC627 comprises the new MSP-1$_{42}$ gene modified in accordance with the invention, GTC479 is the construct comprising the native MSP-1$_{42}$ gene, and construct GTC469 is a negative control DNA FIG. 5 panel B is a Western analysis wherein the eluted fractions after affinity purifications. Numbers are collected fractions. The results show that fractions from GTC679 the modified MSP-1$_{42}$ synthetic gene construct reacted with polyclonal antibodies to MSP-1 and the negative control GTC479 did not.

FIG. 6 depicts the nucleic acid sequences of OT1 (SEQ ID NO:3), OT2 (SEQ ID NO:4), MSP-8 (SEQ ID NO:5), MSP-2 (SEQ ID NO:6), and MSP1 (SEQ ID NO:7) described in the Examples.

FIG. 11 is a schematic representation of the nucleotide sequence of MSP42-2 (SEQ ID NO:8) and predicted amino acid sequence (SEQ ID NO:11).

DETAILED DESCRIPTION OF THE PREFERRED EMBODIMENTS

Figure 4A:
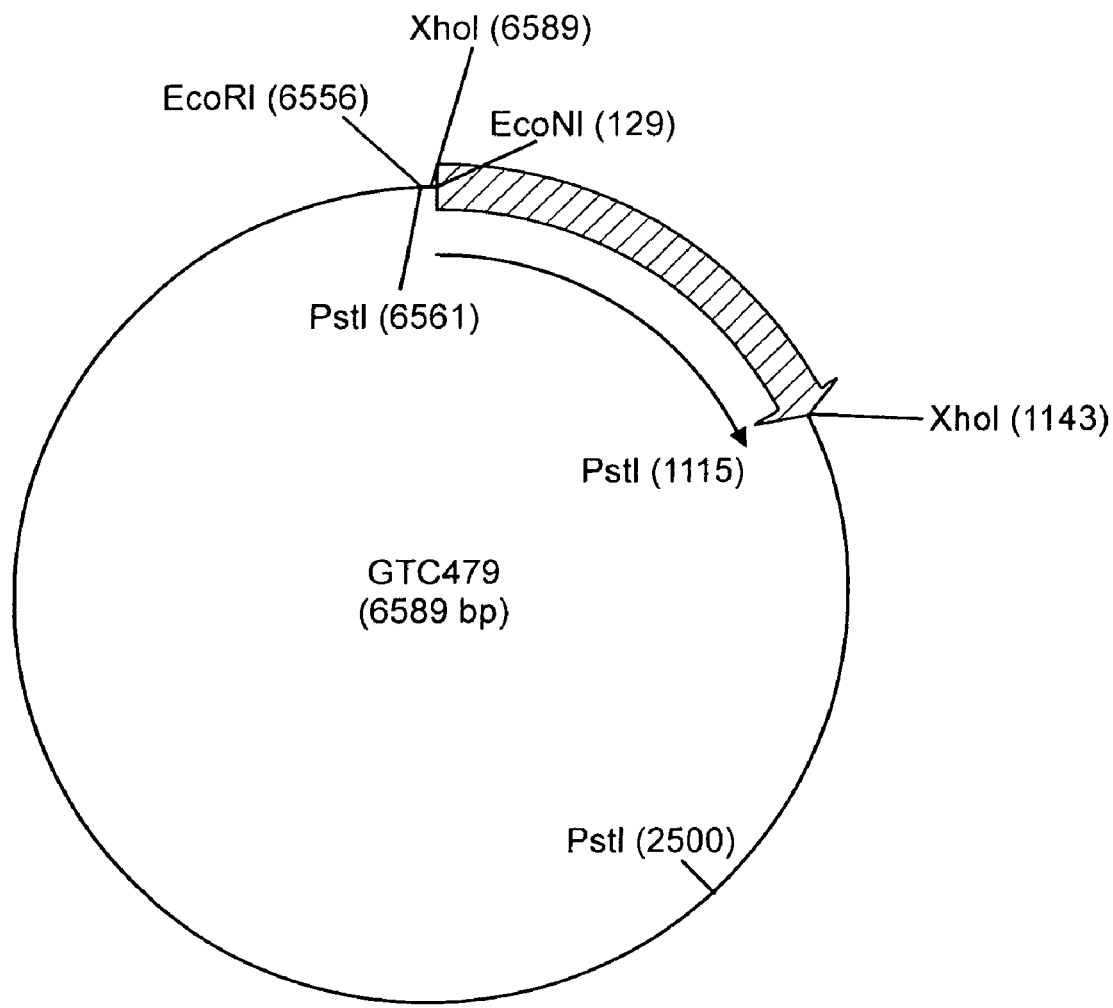
FIGS. 4a-c depict MSP-1$_{42}$ constructs GTC 479, GTC 564, and GTC 627, respectively as are described in the examples.

The patent and scientific literature referred to herein establishes the knowledge that is available to those with skill in the art. The issued US patents, allowed applications, published foreign applications, and references cited herein are hereby incorporated by reference. Any conflicts between these references and the present disclosure shall be resolved in favor of the present disclosure.

The invention provides modified recombinant nucleic acid sequences (preferably DNA) and methods for increasing the mRNA levels and protein expression of proteins which are known to be, or are likely to be, difficult to express in cell culture systems, mammalian cell culture systems, or in transgenic animals. The preferred "difficult" protein candidates for expression using the recombinant techniques of the invention are those proteins derived from heterologous cells preferably those of lower organisms such as parasites, bacteria, and virus, having DNA coding sequences comprising high overall AT content or AT rich regions and/or mRNA instability motifs and/or rare codons relative to the recombinant expression system to be used.

In a first aspect, the invention features a modified known nucleic acid, preferably a gene from a bacterium, virus or parasite, capable of being expressed in a cell system, wherein the modification comprises a reduced AT content, relative to the unmodified sequence, and optionally further comprises elimination of at least one or all mRNA instability motifs present in the natural gene. A "cell system" includes cell culture systems, tissue culture systems, organ culture systems and tissues of living animals. In certain preferred embodiments the modification further comprises replacement of one or more codons of the natural gene with preferred codons of the cell system. Each of these features are achieved by replacing one or more codons of the natural gene with codons recognizable to, and preferably preferred by the cell system that encode the same amino acid as the codon which was replaced in the natural gene. In accordance with the invention, such "silent" nucleotide and codon substitutions should be sufficient to achieve the goal lowering AT content and/or of eliminating mRNA instability motifs, and/or reducing the number of rare codons, while maintaining, and preferably improving the ability of the cell system to produce mRNA and express the desired protein.

Also included in the invention are those sequences which are specifically homologous to the modified nucleic acids of the invention under suitable stringent conditions, specifically excluding the known nucleic acids from which the modified nucleic acids are derived. A sequence is "specifically homologous" to another sequence if it is sufficiently homologous to specifically hybridize to the exact complement of the sequence. A sequence "specifically hybridizes" to another sequence if it hybridizes to form Watson-Crick or Hoogsteen base pairs either in the body, or under conditions which approximate physiological conditions with respect to ionic strength, e.g., 140 mM NaCl, 5 mM MgCl$_2$. Preferably, such specific hybridization is maintained under stringent conditions, e.g., 0.2×SSC at 68° C.

In preferred embodiments, the nucleic acid of the invention is capable of expressing the protein in mammalian cell culture, or in a transgenic animal at a level which is at least 25%, and preferably 50% and even more preferably at least 100% or more of that expressed by the natural gene in an in vitro cell culture system or in a transgenic animal under identical conditions (i.e. the same cell type, same culture conditions, same expression vector).

As used herein, the term "expression" is meant mRNA transcription resulting in protein expression. Expression may be measured by a number of techniques known in the art including using an antibody specific for the protein of interest. By "natural gene" or "native gene" is meant the gene sequence, or fragments thereof (including naturally occurring allelic variations), which encode the wild type form of the protein and from which the modified nucleic acid is derived. A "preferred codon" means a codon which is used more prevalently by the cell system of choice. Not all codon changes described herein are changes to a preferred codon, so long as the codon replacement is a codon which is at least recognized by the cell system. The term "reduced AT content" as used herein means having a lower overall percentage of nucleotides having A (adenine) or T (thymine) bases relative to the natural gene due to replacement of the A or T containing nucleotide positions or A and/or T containing codons with nucleotides or codons recognized by the cell system of choice and which do not change the amino acid sequence of the target protein. "Heterologous" is used herein to denote genetic material originating from a different species than that into which it has been introduced, or a protein produced from such genetic material.

Particularly preferred cell systems of the invention include mammalian cell culture systems such as COS cells and CHO cells, as well as transgenic animals, particularly the mammary tissue of transgenic animals. However, the invention also contemplates bacteria, yeast, *E. coli*, and viral expression systems such as baculovirus and even plant systems.

In a second aspect, the invention provides a process for preparing a modified nucleic acid of the invention comprising the steps of lowering the overall AT content of the natural gene encoding the protein, and/or eliminating at least one or all mRNA instability motifs and/or replacing one or more codons with a preferred codon of the cell system of choice, all by replacing one or more codons in the natural gene with codons recognizable to, and preferably with codons preferred by the cell system of choice and which code for the same amino acids as the replaced codon. Standard reference works describing the general principals of recombinant DNA technology include Watson, J. D. et al, *Molecular Biology of the Gene*, Volumes I and II the Benjamin/Cummings Publishing Company, Inc. publisher, Menlo Park, Calif. (1987) Darnell, J. E. et al., *Molecular Cell Biology*, Scientific American Books, Inc., Publisher, New York, N.Y. (1986); Old, R. W., et al., *Principles of Gene Manipulation: An Introduction to Genetic Engineering*, 2d edition, University of California Press, Berkeley Calif. (1981); Maniatis, T., et al., *Molecular Cloning: A Laboratory Manual*, $2^{nd}$ ed. Cold Spring Harbor Laboratory, publisher, Cold Spring Harbor, N.Y. (1989) and *Current Protocols in Molecular Biology*, Ausubel et al., Wiley Press, New York, N.Y. (1992). This aspect of the invention further includes modified nucleic acids prepared according to the process of the invention.

Without being limited to any theory, previous research has indicated that a conserved AU sequence (AUUUA) from the 3' untranslated region of GM-CSF mRNA mediates selective mRNA degradation (Shaw, G. and Kamen, R. *Cell* 46:659-667). The focus in the past has been on the presence of these instability motifs in the untranslated region of a gene. The instant invention is the first to recognize an advantage to eliminating the instability sequences in the coding region of a gene.

In a third aspect, the invention also provides vectors comprising nucleic acids of the invention and promoters active in the cell line or organism of choice, and host cells transformed with nucleic acids of the invention. Preferred vectors include an origin of replication and are thus replicatable in one or more cell type. Certain preferred vectors are expression vectors, and further comprise at least a promoter and passive terminator, thereby allowing transcription of the recombinant expression element in a bacterial, fungal, plant, insect or mammalian cell.

In a fourth aspect, the invention provides transgenic expression vectors for the production of transgenic lactating animals comprising nucleic acids of the invention as well as transgenic non-human lactating animals whose germlines comprise a nucleic acid of the invention. Such transgenic expression vectors comprise a promoter capable of being expressed as part of the genome of the host transgenic animal. General principals for producing transgenic animals are known in the art. See for example Hogan et al., *Manipulating the Mouse Embryo: A Laboratory Manual*, Cold Spring Harbor Laboratory, (1986); Simons et al, *Bio/Technology* 6:179-183, (1988); Wall et al., *Biol. Reprod.* 32:645-651, (1985); Buhler et al., *Bio/Technology*, 8:140-143 (1990); Ebert et al., *Bio/Technology* 9:835-838 (1991); Krimenfort et al., *Bio/Technology* 9:844-847 (1991); Wall et al., *J. Cell. Biochem.* 49:113-120 (1992). Techniques for introducing foreign DNA sequences into mammals and their germ cells were originally developed in the mouse. See e.g., Gordon et al., *Proc. Natl. Acad. Sci. USA* 77:7380-7384, (1980); Gordon and Ruddle, *Science* 214: 1244-1246 (1981); Palmiter and Brinster, *Cell* 41: 343-345, 1985; Brinster et al., *Proc Natl. Acad Sci., USA* 82:4438-4442 (1985) and Hogan et al. (ibid.). These techniques were subsequently adapted for use with larger animals including cows and goats. Up until very recently, the most widely used procedure for the generation of transgenic mice or livestock, several hundred linear molecules of the DNA of interest in the form of a transgenic expression construct are injected into one of the pro-nuclei of a fertilized egg. Injection of DNA into the cytoplasm of a zygote is also widely used. Most recently cloning of an entire transgenic cell line capable of injection into an unfertilized egg has been achieved (KHS Campbell et al., *Nature* 380 64-66, (1996)).

In a fifth aspect, the invention provides a transgenic expression vector for production of a transgenic lactating animal species comprising a nucleic acid of the invention, a promoter operatively coupled to the nucleic acid which directs mammary gland expression of the protein encoded by the nucleic acid into the milk of the transgenic animal. The mammary gland expression system has the advantages of high expression levels, low cost, correct processing and accessibility. Known proteins, such as bovine and human alpha-lactalbumin have been produced in lactating transgenic animals by several researchers. (Wright et al, *Bio/Technology* 9:830-834 (1991); Vilotte et al, *Eur. J. Biochem.*, 186:43-48 (1989); Hochi et al., *Mol Reprod. And Devel.* 33:160-164 (1992); Soulier et al., *FEBS Letters* 297(1, 2):13-18 (1992)) and the system has been shown to produce high levels of protein.

Preferred promoters are active in the mammary tissue. Particularly useful are promoters that are specifically active in genes encoding milk specific proteins such as genes found in mammary tissue, i.e. are more active in mammary tissue than in other tissues under physiological conditions where milk is synthesized. Most preferred are promoters that are both specific to and efficient in mammary tissue. Among such promoters, the casein, lactalbumin and lactalglobulin promoters are preferred, including, but not limited to the alpha, beta and gamma casein promoters and the alpha lactalbumin and beta-lactalglobulin promoters. Preferred among the promoters are those from rodent, goats and cows. Other promoters include those that regulate a whey acidic protein (WAP) gene.

In a preferred embodiment of the invention, a modified nucleic acid encoding MSP-1 or fragments thereof capable of expression in a cell culture system, mammalian cell culture system or in the milk of a transgenic animal is provided. Nucleic acid sequences encoding the natural MSP-1 gene are modified in accordance with the invention. First the overall AT content is reduced by replacing codons of the natural gene with codons recognizable to, and preferably with codons preferred by the cell system of choice, that encode the same amino acid but are sufficient to lower the AT content of the modified nucleic acid as compared to the native MSP-1 gene or gene fragment. Second, mRNA instability motifs (AUUUA, Shaw and Kamen, supra) in the native gene or gene fragment are eliminated from the coding sequence of the gene by replacing codons of the natural gene with codons recognizable to, and preferably preferred by the cell system of choice that encode the same amino acid but are sufficient to eliminate the mRNA instability motif. Optionally, any other codon of the native gene may be replaced with a preferred codon of the expression system of choice as described.

In a sixth aspect, the invention provides a DNA vaccine comprising a modified nucleic acid according to the invention. In certain preferred embodiments, the DNA vaccine comprises a vector according to the invention, The DNA vaccine according to the invention may be in the form of a "naked" or purified modified nucleic acid according to the invention, which may or may not be operatively associated with a promoter. A nucleic acid is operatively associated with a promoter if it is associated with the promoter in a manner which allows the nucleic acid sequence to be expressed. Such DNA vaccines may be delivered without encapsulation, or they may be delivered as part of a liposome, or as part of a viral genome. Generally, such vaccines are delivered in an amount sufficient to allow expression of the nucleic acid and elicit an antibody response in an animal, including a human, which receives the DNA vaccine. Subsequent deliveries, at least one week after the first delivery, may be used to enhance the antibody response. Preferred delivery routes include introduction via mucosal membranes, as well as parenteral administration.

A preferred embodiment of this aspect of the invention comprises a fragment of a modified MSP-1 gene according to the invention. Such fragment preferably includes from about 5% to about 100% of the overall gene sequence and comprises one or more modification according to the invention.

Figures 3A, 3B:
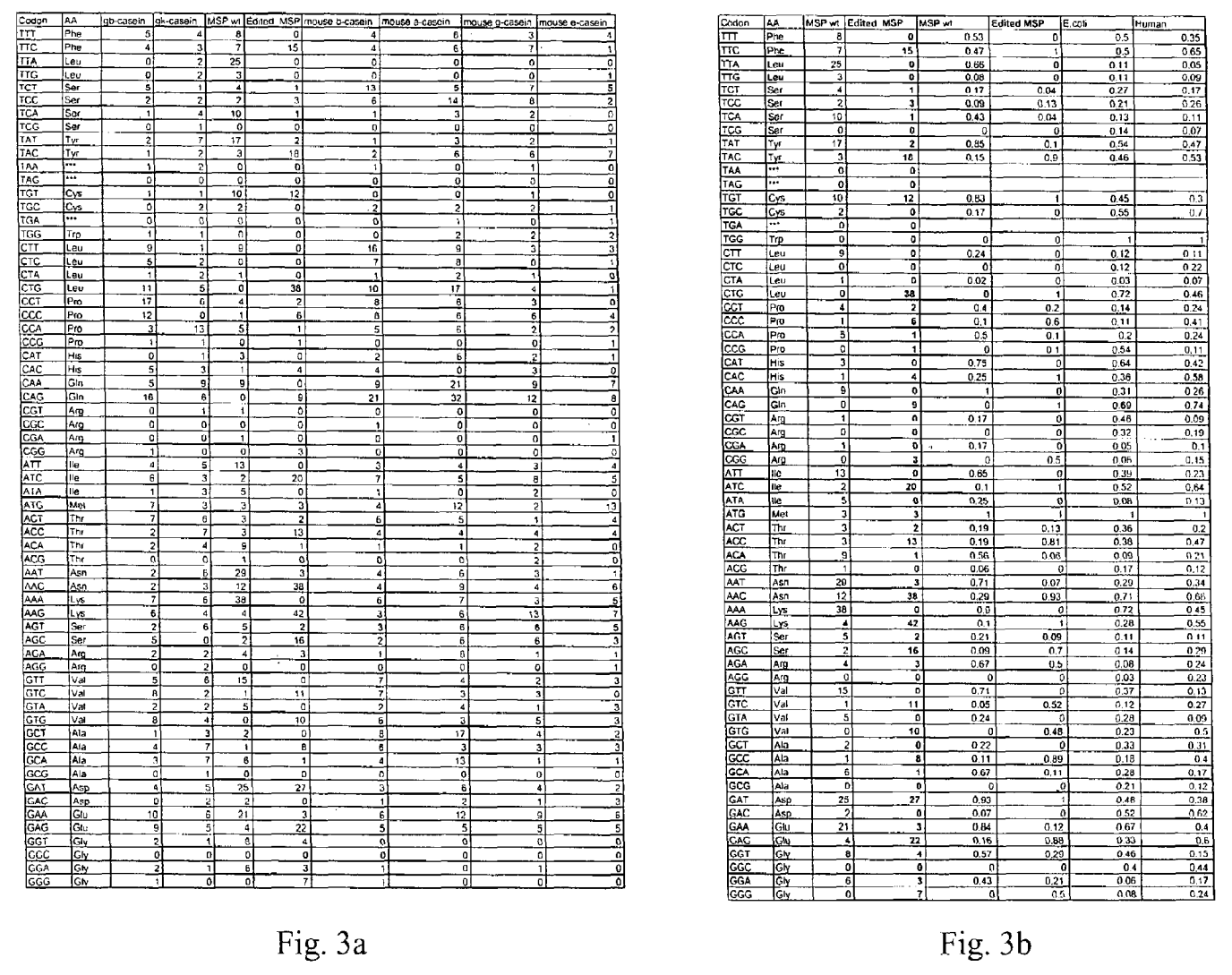

Examples of codon usage from E. coli and human are shown in FIG. 3b. FIG. 3b shows the frequency of codon usage for the MSP-1 native gene as well as the modified MSP-1 gene of the invention and also compares the frequency of codon usage to that of E. coli and human genes. Codon usage frequency tables are readily available and known to those skilled in the art for a number of other expression systems such as yeast, baculovirus and the mammalian, systems.

The following examples illustrate certain preferred modes of making and practicing the present invention, but are not meant to limit the scope of the invention since alternative methods may be utilized to obtain similar results.

EXAMPLES

Creation of Novel Modified MSP-$1_{42}$ Gene

In one embodiment, a novel modified nucleic acid encoding the C-terminal fragment of MSP-1 is provided. The novel, modified nucleic acid of the invention encoding a 42 kD C-terminal part of MSP-1 (MSP-$1_{42}$) capable of expression in mammalian cells of the invention is shown in FIG. 1. The natural MSP-$1_{42}$ gene (FIG. 2) was not capable of being expressed in mammalian cell culture or in transgenic mice Analysis of the natural MSP-$1_{42}$ gene suggested several characteristics that distinguish it from mammalian genes. First, it has a very high overall AT content of 76%. Second, the mRNA instability motif, AUUUA, occurred 10 times in this 1100 bp DNA segment (FIG. 2). To address these differences a new MSP-$1_{42}$ gene was designed. Silent nucleotide substitution was introduced into the native MSP-$1_{42}$ gene at 306 positions to reduce the overall AT content to 49.7%. Each of the 10 AUUUA mRNA instability motifs in the natural gene were eliminated by changes in codon usage as well. To change the codon usage, a mammary tissue specific codon usage table, FIG. 3a, was created by using several mouse and goat mammary specific proteins. The table was used to guide the choice of codon usage for the modified MSP-$1_{42}$ gene as described above. For example as shown in the Table in FIG. 3a, in the natural gene, 65% (25/38) of the Leu was encoded by TTA, a rare codon in the mammary gland. In the modified MSP-$1_{42}$ gene, 100% of the Leu was encoded by CTG, a preferred codon for Leu in the mammary gland.

Figure 4B:
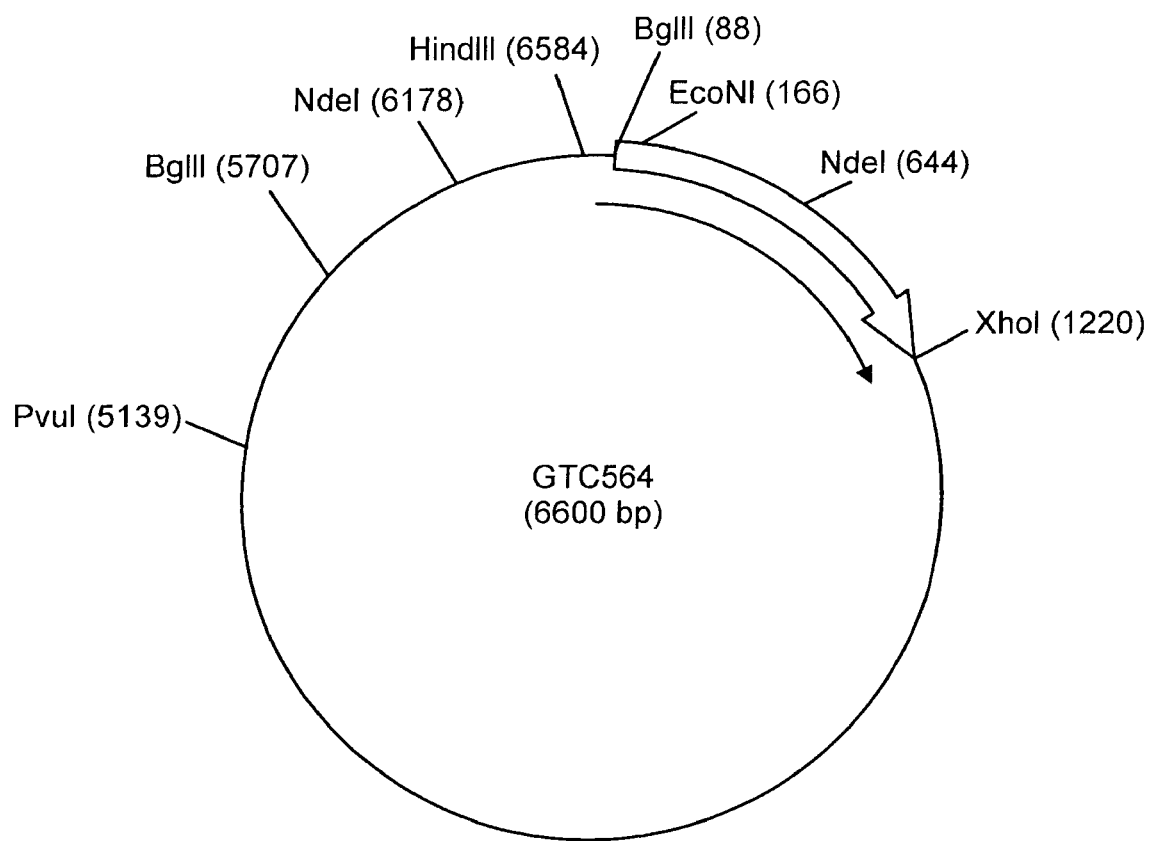
Figure 4C:
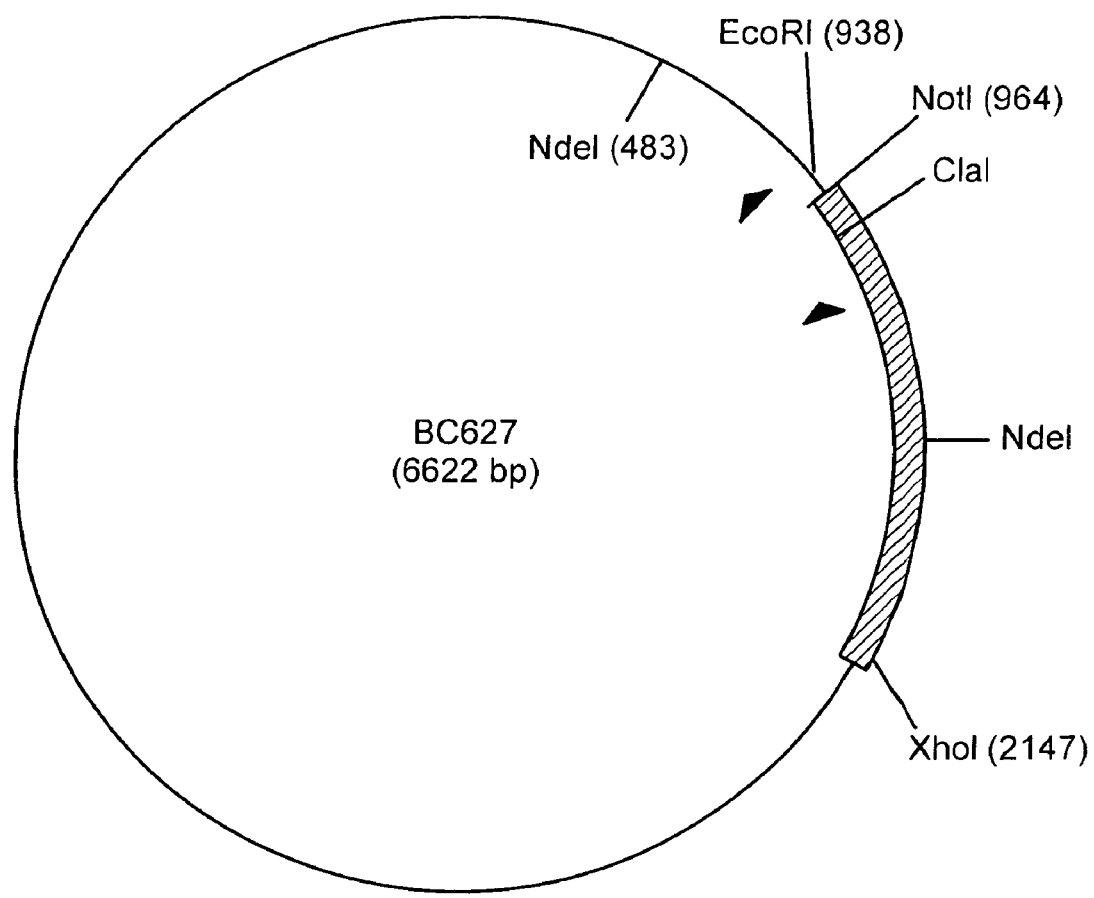

An expression vector was created using the modified MSP-$1_{42}$ gene by fusing the first 26 amino acids of goat beta-casein to the N-terminal of the modified MSP-$1_{42}$ gene and a SalI-XhoI fragment which carries the fusion gene was subcloned into the XhoI site of the expression vector pCDNA3. A His6 tag was fused to the 3' end of the MSP-$1_{42}$ gene to allow the gene product to be affinity purified. This resulted in plasmid GTC627 (FIG. 4c).

To compare the natural MSP-$1_{42}$ gene construct to the modified MSP-$1_{42}$ nucleic acid of the invention, an expression vector was also created for the natural MSP-$1_{42}$ gene and the gene was added to mammalian cell culture and injected into mice to form transgenic mice as follows:

Construction of the Native MSP-$1_{42}$ Expression Vector

To secrete the truncated the merozoite surface protein-1 (MSP-1) of Plasmodium falciparum, the wild type gene encoding the 42 KD C-terminal part of MSP-1 (MSP-$1_{42}$) was fused to either the DNA sequence that encodes the first 15 or the first 25 amino acids of the goat beta-casein. This is achieved by first PCR amplify the MSP-1 plasmid (received from Dr. David Kaslow, NIH) with primers MSP1 and MSP2 (FIG. 6), then cloned the PCR product into the TA vector (Invitrogen). The BglII-XhoI fragments of the PCR product was ligated with oligos OT1 and OT2 (FIG. 6) into the expression vector pCDNA3. This yielded plasmid GTC564 (FIG. 4b), which encodes the 15 amino acid beta-casein signal peptide and the first 11 amino acids of the mature goat beta-casein followed by the native MSP-$1_{42}$ gene. Oligos MSP-8 and MSP-2 (FIG. 6) were used to amplify MSP-1 plasmid by PCR, the product was then cloned into TA vector. The XhoI fragment was exercised and cloned into the XhoI site of the expression vector pCDNA3 to yield plasmid GTC479 (FIG. 4a), which encoded 15 amino acid goat beta-casein signal peptide fused to the wild-type MSP-$1_{42}$ gene. A His6 tag was added to the 3' end of MSP-$1_{42}$ gene in GTC 564 and GTC 479.

Native MSP-$1_{42}$ Gene is not Expressed in COS-7 Cells

Expression of the native MSP gene in cultured COS-7 cells was assayed by transient transfection assays. GTC479 and GTC564 plasmids DNA were introduced into COS-7 cells by lipofectamine (Gibco-BRL) according to manufacturer's protocols. Total cellular RNA was isolated from the COS cells two days post-transfection. The newly synthesized proteins were metabolically labeled for 10 hours by adding $^{35}$S methionine added to the culture media two days-post transfection.

To determine the MSP mRNA expression in the COS cells, a Northern blot was probed with a $^{32}$P labeled DNA fragment from GTC479. No MSP RNA was detected in GTC479 or GTC564 transfectants (data not shown). Prolonged exposure revealed residual levels of degraded MSP mRNA. The $^{35}$S labeled culture supernatants and the lysates were immunoprecipitated with a polyclonal antibody raised against MSP. Immunoprecipitation experiments showed that no expression from either the lysates or the supernatants of the GTC479 or GTC564 transfected cells (data not shown). These results showed that the native MSP-1 gene was not expressed in COS cells.

Figure 7:
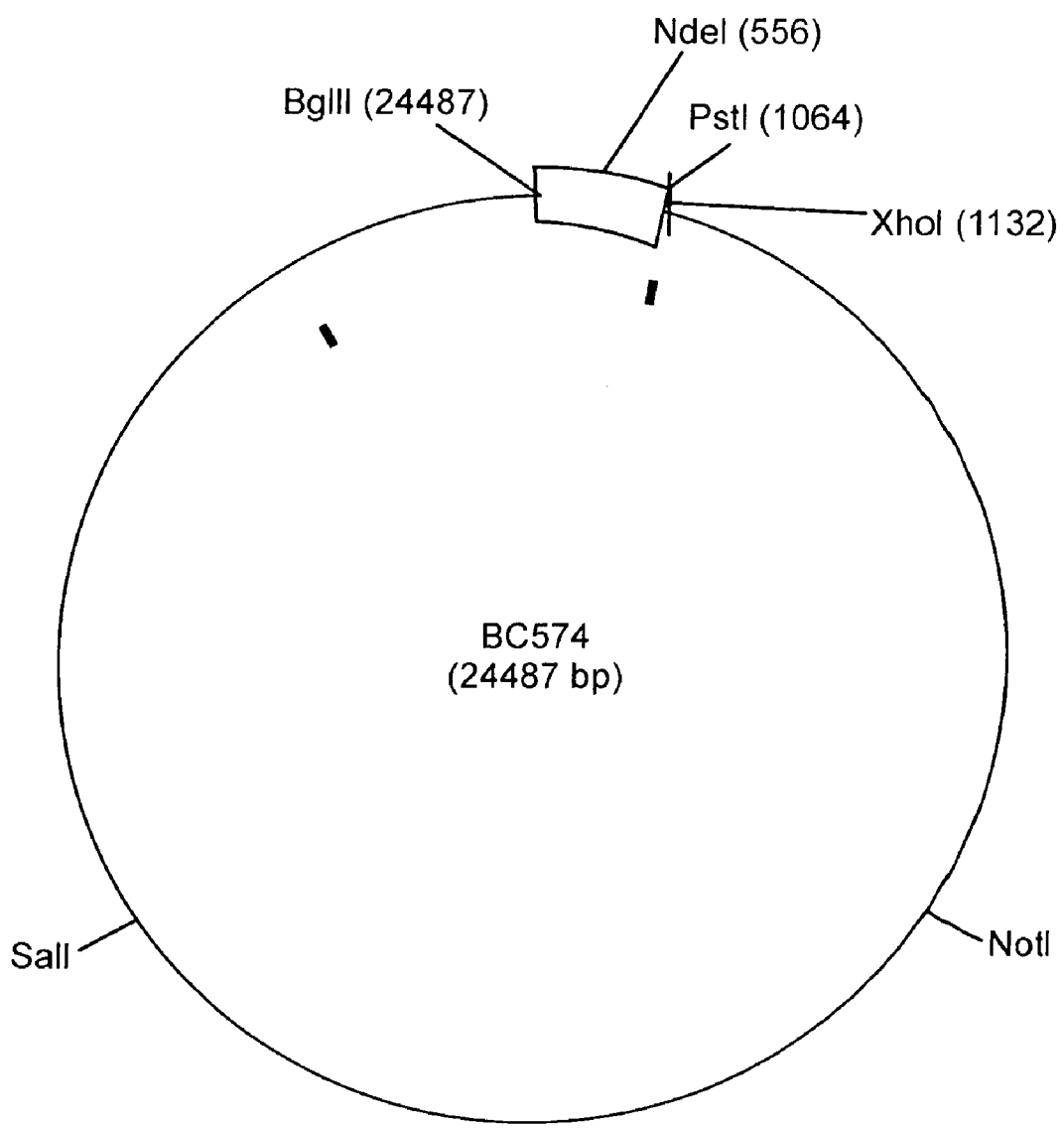
FIG. 7 is a schematic representation of plasmid BC574.

Native MSP-$1_{42}$ Gene is not Expressed in the Mammary Gland of Transgenic Mice The SalI-XhoI fragment of GTC479, which encoded the 15 amino acids of goat beta-casein signal peptide, the first 11 amino acids of goat beta-casein, and the native MSP-$1_{42}$ gene, was cloned into the XhoI site of the beta-casein expressed in vector BC350. This yielded plasmid BC574 (FIG. 7). A SalI-NotI fragment of BC574 was injected into the mouse embryo to generate transgenic mice. Fifteen lines of transgenic mice were established. Milk from the female founder mice was collected and subjected to Western analysis with polyclonal antibodies against MSP. None of the seven mice analyzed were found to express MSP-1$_{42}$ protein in their milk. To further determine if the mRNA of MSP-1$_{42}$ was expressed in the mammary gland, total RNA was extracted from day 11 lactating transgenic mice and analyzed by Northern blotting. No MSP-1$_{42}$ mRNA was detected by any of the BC 574 lines analyzed. Therefore, the MSP-1$_{42}$ transgene was not expressed in the mammary gland of transgenic mice. Taken together, these experiments suggest that native parasitic MSP-1$_{42}$ gene could not be expressed in mammalian cells, and the block is as the level of mRNA abundance.

Expression of MSP in the Mammalian Cells

Transient transfection experiments were performed to evaluate the expression of the modified MSP-1$_{42}$ gene of the invention in COS cells. GTC627 and GTC479 DNA were introduced into the COS-7 cells. Total RNA was isolated 48 hours post-transfection for Northern analysis. The immobilized RNA was probed with $^{32}$P labeled SalI-XhoI fragment of GTC627. A dramatic difference was observed between GTC479 and GTC627. While no MSP-1$_{42}$ mRNA was detected in the GTC479 transfected cells as shown previously, abundant MSP-1$_{42}$ mRNA was expressed by GTC627 (FIG. 5, Panel A). GTC 469 was used as a negative control and comprises the insert of GTC564 cloned into cloning vector PU19, a commercially available cloning vector. A metabolic labeling experiment with $^{35}$S methionine followed by immunoprecipitation with polyclonal antibody (provided by D. Kaslow NIAID, NIH) against MSP showed that MSP-1$_{42}$ protein was synthesized by the transfected COS cells (FIG. 5, Panel B). Furthermore, MSP-1$_{42}$ was detected in the transfected COS supernatant, indicating the MSP-1$_{42}$ protein was also secreted. Additionally, using Ni-NTA column, MSP-1$_{42}$ was affinity purified from the GTC627 transfected COS supernatant.

These results demonstrated that the modification of the parasitic MSP-1$_{42}$ gene lead to the expression of MSP mRNA in the COS cells. Consequently, the MSP-1$_{42}$ product was synthesized and secreted by mammalian cells.

Polyclonal antibodies used in this experiment may also be prepared by means well known in the art (*Antibodies: A Laboratory Manual*, Ed Harlow and David Lane, eds. Cold Spring Harbor Laboratory, publishers (1988)). Production of MSP serum antibodies is also described in Chang et al., *Infection and Immunity* (1996) 64:253-261 and Chang et al., (1992) *Proc Natl. Acad. Sci. USA* 86:6343-6347.

The results of this analysis indicate that the modified MSP-1$_{42}$ nucleic acid of the invention is expressed at a very high level compared to that of the natural protein which was not expressed at all. These results represent the first experimental evidence that reducing the AT % in a gene leads to expression of the MSP gene in heterologous systems and also the first evidence that removal of AUUUA mRNA instability motifs from the MSP coding region leads to the expression of MSP protein in COS cells.

Thus, the data presented here suggest that certain heterologous proteins that may be difficult to express in cell culture or transgenic systems because of high AT content and/or the presence of instability motifs, and or the usage of rare codons which are unrecognizable to the cell system of choice may be reengineered to enable expression in any given system with the aid of codon usage tables for that system. The present invention represents the first time that a DNA sequence has been modified with the goal of removing suspected sequences responsible for degradation resulting in low RNA levels or no RNA at all. The results shown in the FIG. 5, Panel A Northern (i.e. no RNA with native gene and reasonable levels with a modified DNA sequence in accordance with the invention), likely explains the increase in protein production.

The following examples describe the expression of MSP1-42 as a native non-fusion (and non-glycosylated) protein in the milk of transgenic mice.

Construction of MSP Transgene

Figure 8:
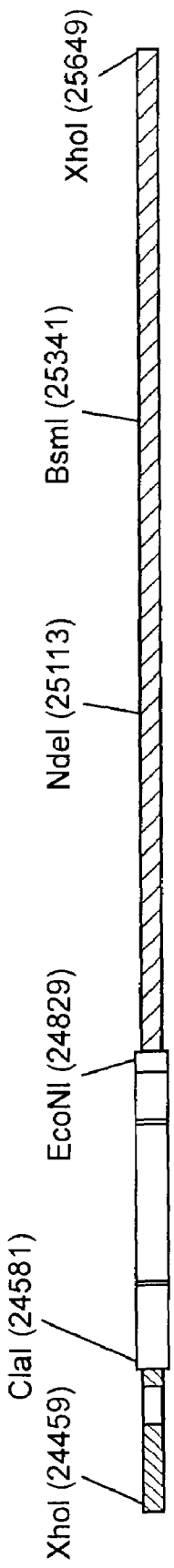
FIG. 8 is a schematic representation of BC620.
Figure 9:
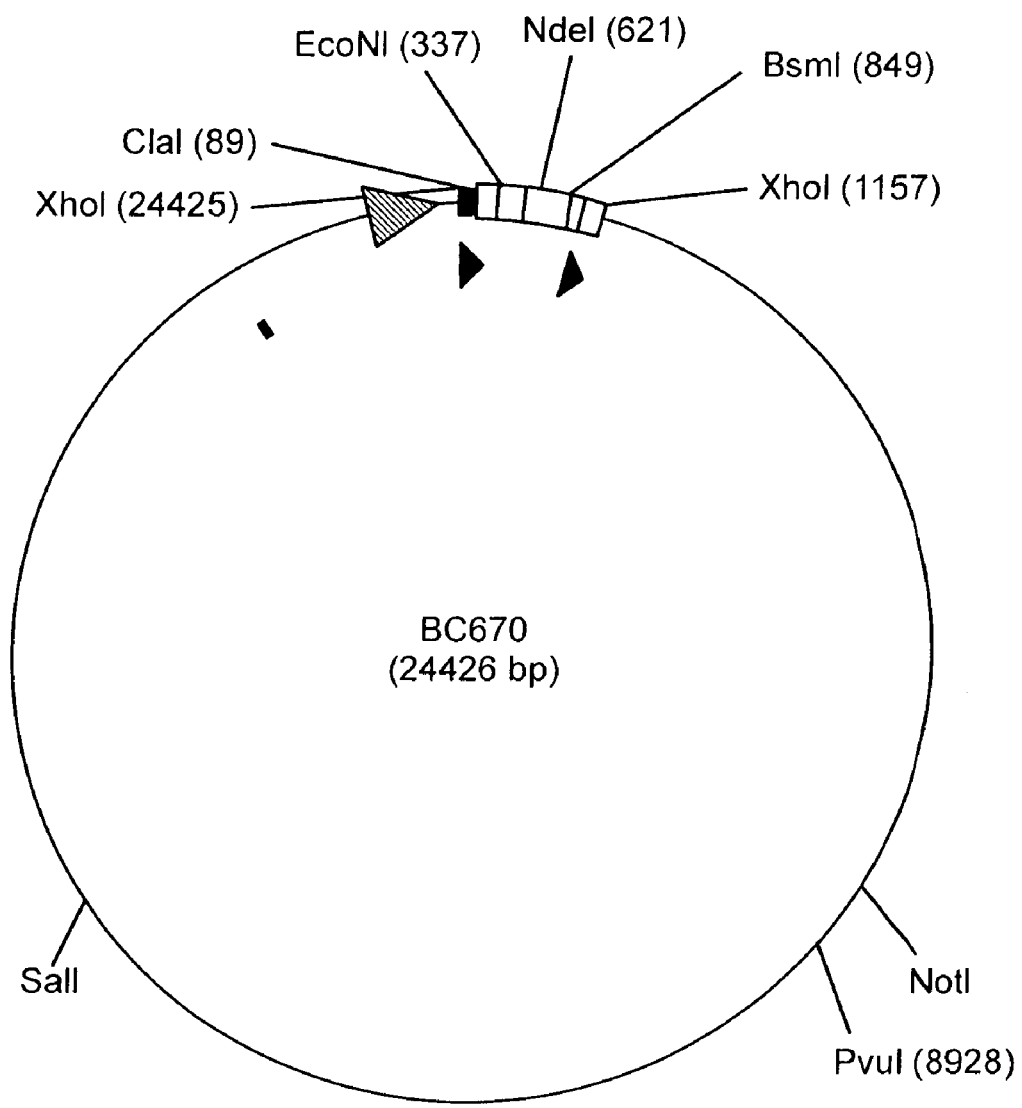
FIG. 9 is a schematic representation of BC670.

To fuse MSP1-42 to the 15 amino acid β-casein signal peptide, a pair of oligos, MSP203 and MSP204 (MSP203: ggccgctcgacgccaccatgaaggtcct-cataattgcctgtctggtggctctggccatt gcagccgtcactccctccgtcat (SEQ ID NO: 12), MSP204: cgatgacggagggagtgacggctg-caatggccagagcca ccagacaggcaattatgaggacct-tcatggtggcgtcgagc (SEQ ID NO:13)), which encode the 15 amino acid—casein signal and the first 5 amino acid of the MSP1-42 ending at the Cla I site, was ligated with a Cla I-Xho I fragment of BC620 (FIG. 8) which encodes the rest of the MSP1-42 gene, into the Xho I site of the expression vector pCDNA3. A Xho I fragment of this plasmid (GTC669) was then cloned into the Xho I site of milk specific expression vector BC350 to generate B670 (FIG. 9).

Expressing of MSP1-42 in the Milk of Transgenic Mice

Figure 10:
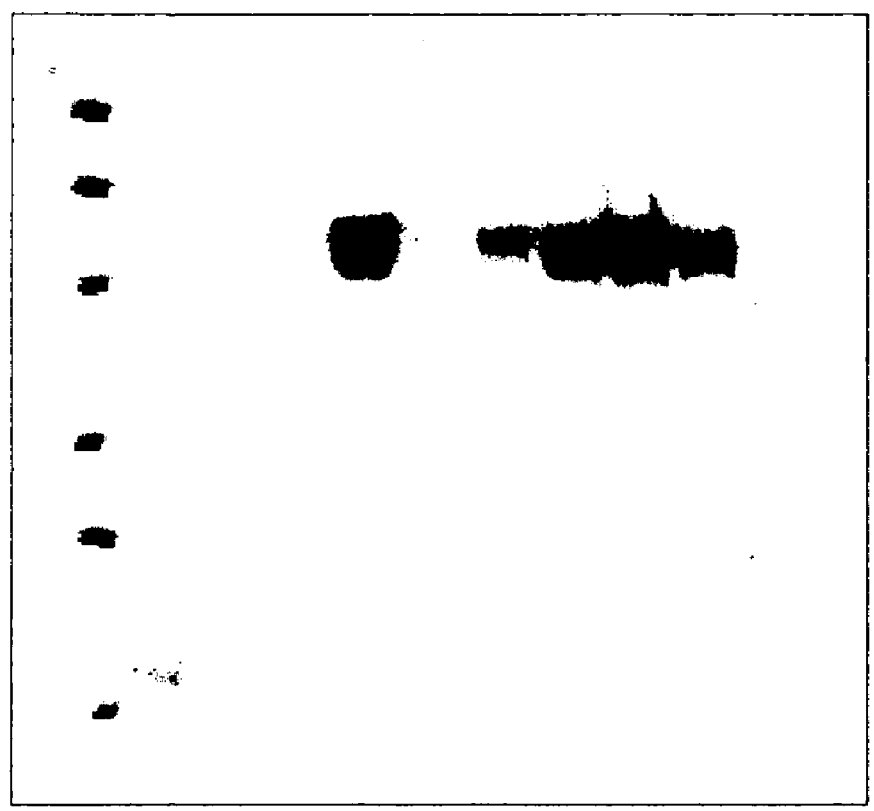
FIG. 10 is a representation of a Western blot of MSP in transgenic milk.

A Sal I-Not I fragment was prepared from plasmid BC670 and microinjected into the mouse embryo to generate transgenic mice. Transgenic mice were identified by extracting mouse DNA from tail biopsy followed by PCR analysis using oligos GTC17 and MSP101 (sequences of oligos: GTC17, GATTGACAAGTAATACGCTGTTTCCTC (SEQ ID NO:14), Oligo MSP101, GGATTCAATAGATACGG (SEQ ID NO:15)). Milk from the female founder transgenic mice was collected at day 7 and day 9 of lactation, and subjected to western analysis to determine the expression level of MSP-1-42 using a polyclonal anti-MSP antibody and monoclonal anti-MSP antibody 5.2 (Dr. David Kaslow, NIH). Results indicated that the level of MSP-1-42 expression in the milk of transgenic mice was at 1-2 mg/ml (FIG. 10).

Construction of MSP1-42 Glycosylation Sites Minus Mutants

Our analysis of the milk produced MSP revealed that the transgenic MSP protein was N-glycosylated. To eliminate the N-glycosylation sites in the MSP1-42 gene, Asn (N) at positions 181 and 263 were substituted with Gln (Q). The substitutions were introduced by designing DNA oligos that anneal to the corresponding region of MSP1 and carry the AAC to CAG mutations. These oligos were then used as PCR primers to produce DNA fragments that encode the N to Q substitutions.

To introduce N262-Q mutation, a pair of oligos, MSPGY-LYCO-3 (CAGGGAATGCTGCAGATCAGC; SEQ ID NO:16) and MSP42-2 (AATTCTCGAGTTAGTGGTG-GTGGTGGTGGTGATCGCAGAAAATACCATG; SEQ ID NO:17, FIG. 11), were used to PCR amplify plasmid GTC627, which contains the synthetic MSP1-42 gene. The PCR product was cloned into pCR2.1 vector (Invitrogen). This generated plasmid GTC716.

To introduce N181-Q mutation, oligos MSPGLYCO-1 (CTCCTTGTTCAGG AACTTGTAGGG; SEQ ID NO:18) and MSPGLCO-2 (GTCCTGCAGTACACATATGAG (SEQ ID NO:19), FIG. 4) were used to amplify plasmid GTC 627. The PCR product was cloned into pCR2.1. This generated plasmid GTC700.

The MSP double glycosylation mutant was constructed by the following three steps: first, a Xho I-Bsm I fragment of BC670 and the Bsm 1-Xho I fragment of GTC716 is ligated into the Xho I site of vector pCR2.1. This resulted a plasmid that contain the MSP-1-42 gene with N262-Q mutation.

Figure 12:
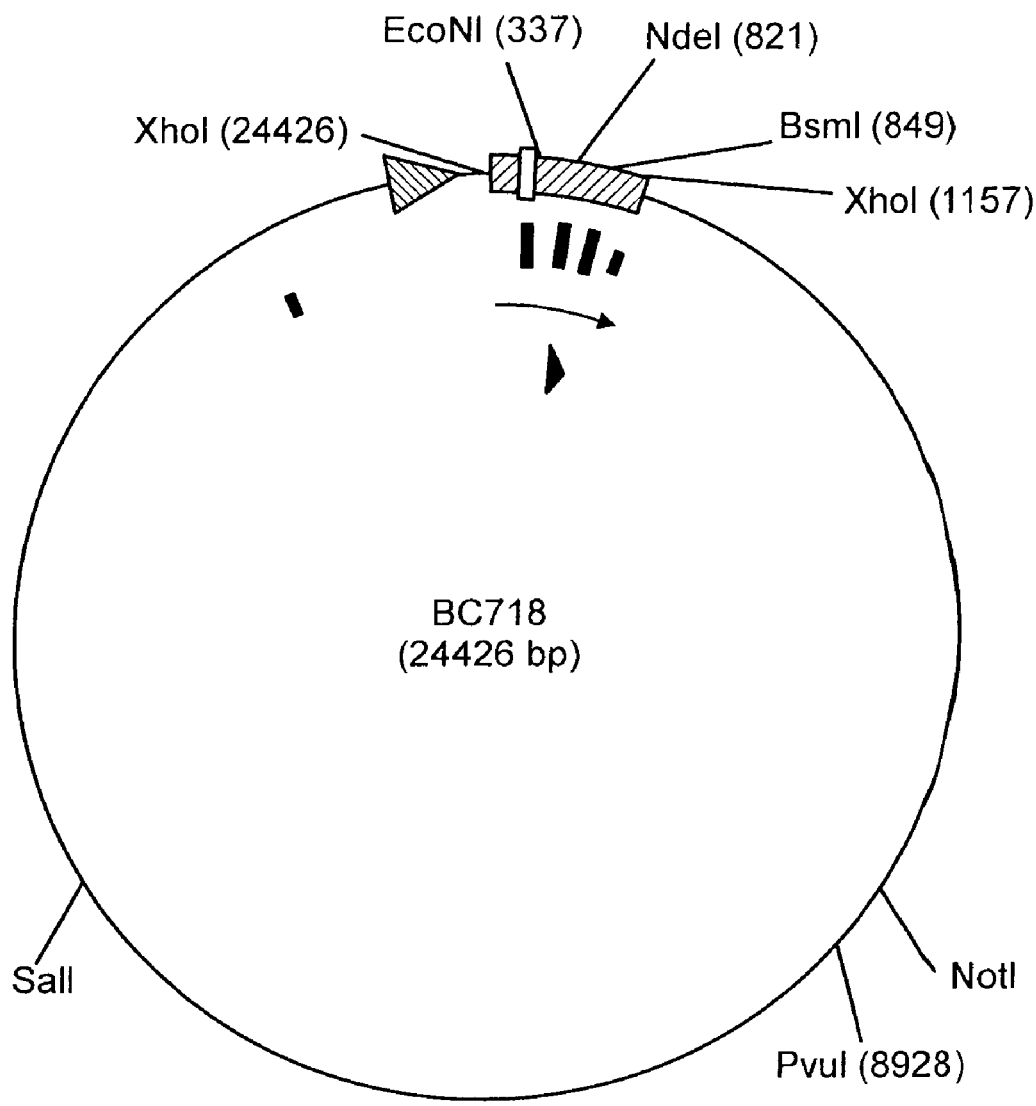
FIG. 12 is a schematic representation of the BC-718.

EcoN I-Nde I fragment of this plasmid was then replaced by the EcoN I-Nde I fragment from plasmid GTC716 to introduce the second mutation, N181-Q. A Xho I fragment of this plasmid was finally cloned into BC350 to generate BC718 (FIG. 12).

Expression of Nonglycosylated MSP1 in Transgenic Animals

BC718 has the following characteristics: it carries the MSP1-42 gene under the control of the β-casein promoter so it can be expressed in the mammary gland of the transgenic animal during lactation. Further, it encodes a 15 amino acid β-casein leader sequence fused directly to MSP1-42, so that the MSP1-42, without any additional amino acid at its N-terminal, can be secreted into the milk. Finally, because the N-Q substitutions, the MSP produced in the milk of the transgenic animal by this construct will not be N-glycosylated. Taken together, the transgenic MSP produced in the milk by BC718 is the same as the parasitic MSP.

Figure 13:
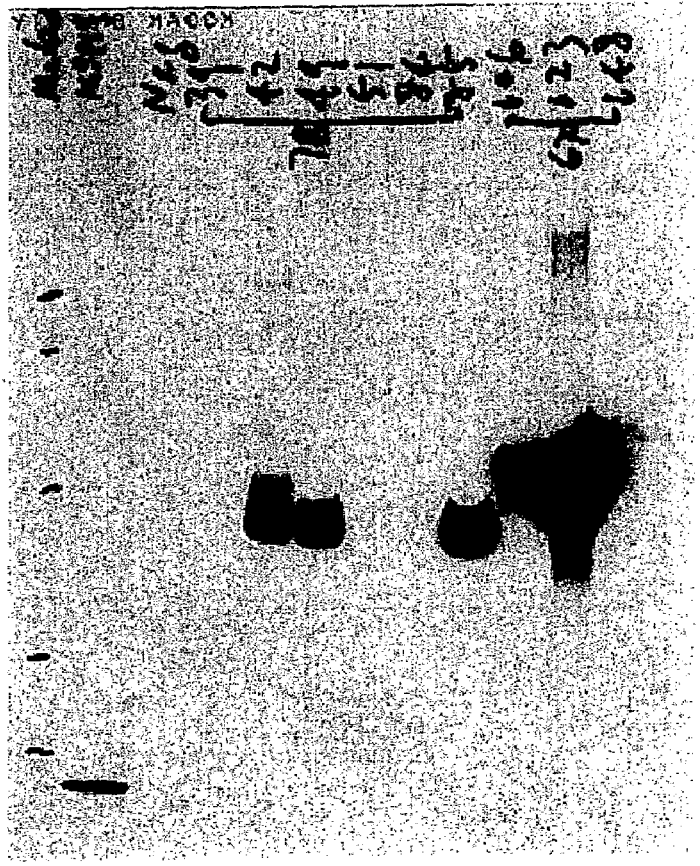
FIG. 13 is a representation of a Western blot of BC-718 expression in transgenic milk.

A SalI/XhoI fragment was prepared from plasmid BC718 and microinjected into mouse embryos to generate transgenic mice. Transgenic animals were identified as described previously. Milk from female founders was collected and analyzed by Western blotting with antibody 5.2. The results, shown in FIG. 13, indicate expression of nonglycosylated MSP1 at a concentration of 0.5 to 1 mg/ml.

EQUIVALENTS

Those skilled in the art will recognize, or be able to ascertain, using no more than routine experimentation, numerous equivalents are considered to be within the scope of this invention, and are covered by the following claims.

What is claimed is:

1. A method for producing *Plasmodium falciparum* protein MSP-1 in milk of a non-human transgenic mammal, comprising:

1) providing a non-human transgenic mammal whose genome comprises a modified nucleic acid sequence encoding said MSP-1 operably linked to a promoter which directs expression in a mammary gland and a signal sequence directing secretion of said MSP-1 into milk, wherein said modified nucleic acid sequence has been modified by replacing a number of AT-containing codons of a nucleic acid sequence encoding said MSP-1, as it naturally occurs in *Plasmodium falciparum*, with a codon or codons preferred by a mammalian cell for the purpose of expression and encoding the same amino acid as the replaced AT-containing codon or codons, wherein the number of codons replaced is sufficient to allow expression of said MSP-1 in said non-human transgenic mammal; and 2) allowing said non-human transgenic mammal to express said MSP-1 in its milk.

2. A method for producing *Plasmodium falciparum* protein MSP-1 in milk of a non-human transgenic mammal, comprising:

1) providing a non-human transgenic mammal whose genome comprises a modified nucleic acid sequence encoding said MSP-1 operably linked to a promoter which directs expression in a mammary gland and a signal sequence directing secretion of said MSP-1 into milk, wherein said modified nucleic acid sequence has been modified by introduction of one or more silent mutations into a number of AUUUA mRNA instability motifs, as they naturally occur in *Plasmodium falciparum*, thereby eliminating said number of AUUUA instability motifs, allowing expression of said MSP-1 in said non-human transgenic mammal; and 2) allowing said non-human transgenic mammal to express said MSP-1 in its milk.

3. A method for producing *Plasmodium falciparum* protein MSP-1 in milk of a non-human transgenic mammal, comprising:

1) providing a non-human transgenic mammal whose genome comprises a modified nucleic acid sequence encoding said MSP-1 operably linked to a promoter which directs expression in a mammary gland and a signal sequence directing secretion of said MSP-1 into milk, wherein said modified nucleic acid sequence has been modified by:

a) replacing a number of AT-containing codons of a nucleic acid sequence encoding said MSP-1, as it naturally occurs in *Plasmodium falciparum*, with a codon or codons preferred by a mammalian cell for the purpose of expression and encoding the same amino acid as the replaced AT-containing codon or codons, and b) introduction of one or more silent mutations into a number of AUUUA mRNA instability motifs, as they naturally occur in *Plasmodium falciparum*, thereby eliminating said AUUUA instability motifs, wherein the number of said modifications is sufficient to allow expression of said MSP-1 in said non-human transgenic mammal; and 2) allowing said non-human transgenic mammal to express said MSP-1 in its milk.

4. The method of claim 1, 2 or 3 wherein the modified nucleic acid further comprises at least one substitution of a glutamine codon for an asparagine codon, resulting in the loss of at least one N-glycosylation site in said MSP-1.

5. A non-human transgenic mammal whose genome comprises a modified nucleic acid sequence encoding *Plasmodium falciparum* protein MSP-1 operably linked to a promoter which directs expression in a mammary gland and a signal sequence directing secretion of said MSP-1 into milk, wherein said modified nucleic acid sequence has been modified by replacing a number of AT-containing codons of a nucleic acid sequence encoding said MSP-1, as it naturally occurs in *Plasmodium falciparum*, with a codon or codons preferred by a mammalian cell for the purposes of expression and encoding the same amino acid as the replaced AT-containing codon or codons, wherein the number of codons replaced is sufficient to allow expression of said MSP-1 in said non-human transgenic mammal, and wherein said non-human transgenic mammal expresses said MSP-1 in its milk.

6. A non-human transgenic mammal whose genome comprises a modified nucleic acid sequence encoding *Plasmodium falciparum* protein MSP-1 operably linked to a promoter which directs expression in a mammary gland and a signal sequence directing secretion of said MSP-1 into milk, wherein said modified nucleic acid sequence has been modified by introduction of one or more silent mutations into a number of AUUUA mRNA instability motifs, as they naturally occur in *Plasmodium falciparum*, thereby eliminating said AUUUA instability motifs, allowing expression of said MSP-1 in said non-human transgenic mammal, and wherein said non-human transgenic mammal expresses said MSP-1 in its milk.

7. The non-human transgenic mammal of claim 6 wherein said modified nucleic acid sequence is further modified by introduction of one or more silent mutations into a number of AUUUA mRNA instability motifs, as they naturally occur in *Plasmodium falciparum*, thereby eliminating said AUUUA instability motifs, and allowing expression of said MSP-1.

8. The non-human transgenic mammal of claim 5, 6, or 7 wherein the modified nucleic acid further comprises at least one substitution of a glutamine codon for an asparagine codon, resulting in the loss of at least one N-glycosylation site in said MSP-1.

\* \* \* \* \*

SEQUENCE LISTING

```
<160> NUMBER OF SEQ ID NOS: 19

<210> SEQ ID NO 1
<211> LENGTH: 1065
<212> TYPE: DNA
<213> ORGANISM: Artificial Sequence
<220> FEATURE:
<223> OTHER INFORMATION: altered MSP sequence; preferably, a bacterium,
      virus, or parasite
<221> NAME/KEY: CDS
<222> LOCATION: (1)...(1065)

<400> SEQUENCE: 1 gcc gtc act ccc tcc gtc atc gat aac atc ctg tcc aag atc gag aac         48
Ala Val Thr Pro Ser Val Ile Asp Asn Ile Leu Ser Lys Ile Glu Asn
 1               5                  10                  15 gag tac gag gtg ctg tac ctg aag ccg ctg gca ggg gtc tac cgg agc         96
Glu Tyr Glu Val Leu Tyr Leu Lys Pro Leu Ala Gly Val Tyr Arg Ser
             20                  25                  30 ctg aag aag cag ctg gag aac aac gtg atg acc ttc aac gtg aac gtg        144
Leu Lys Lys Gln Leu Glu Asn Asn Val Met Thr Phe Asn Val Asn Val
         35                  40                  45 aag gat atc ctg aac agc cgg ttc aac aag cgg gag aac ttc aag aac        192
Lys Asp Ile Leu Asn Ser Arg Phe Asn Lys Arg Glu Asn Phe Lys Asn
     50                  55                  60 gtg ctg gag agc gat ctg atc ccc tac aag gat ctg acc agc agc aac        240
Val Leu Glu Ser Asp Leu Ile Pro Tyr Lys Asp Leu Thr Ser Ser Asn
 65                  70                  75                  80 tac gtg gtc aag gat ccc tac aag ttc ctg aac aag gag aag aga gat        288
Tyr Val Val Lys Asp Pro Tyr Lys Phe Leu Asn Lys Glu Lys Arg Asp
                 85                  90                  95 aag ttc ctg agc agt tac aac tac atc aag gat agc att gat acc gat        336
Lys Phe Leu Ser Ser Tyr Asn Tyr Ile Lys Asp Ser Ile Asp Thr Asp
            100                 105                 110 atc aac ttc gcc aac gat gtc ctg gga tac tac aag atc ctg tcc gag        384
Ile Asn Phe Ala Asn Asp Val Leu Gly Tyr Tyr Lys Ile Leu Ser Glu
        115                 120                 125 aag tac aag agc gat ctg gat tca atc aag aag tac atc aac gat aag        432
Lys Tyr Lys Ser Asp Leu Asp Ser Ile Lys Lys Tyr Ile Asn Asp Lys
    130                 135                 140 cag gga gag aac gag aag tac ctg ccc ttc ctg aac aac atc gag acc        480
Gln Gly Glu Asn Glu Lys Tyr Leu Pro Phe Leu Asn Asn Ile Glu Thr
145                 150                 155                 160 ctg tac aag acc gtc aac gat aag att gat ctg ttc gtg atc cac ctg        528
```

-continued

```
Leu Tyr Lys Thr Val Asn Asp Lys Ile Asp Leu Phe Val Ile His Leu
            165                 170                 175 gag gcc aag gtc ctg aac tac aca tat gag aag agc aac gtg gag gtc    576
Glu Ala Lys Val Leu Asn Tyr Thr Tyr Glu Lys Ser Asn Val Glu Val
            180                 185                 190 aag atc aag gag ctg aat tac ctg aag acc atc cag gat aag ctg gcc    624
Lys Ile Lys Glu Leu Asn Tyr Leu Lys Thr Ile Gln Asp Lys Leu Ala
            195                 200                 205 gat ttc aag aag aac aac aac ttc gtc ggg atc gcc gat ctg agc acc    672
Asp Phe Lys Lys Asn Asn Asn Phe Val Gly Ile Ala Asp Leu Ser Thr
        210                 215                 220 gat tac aac cac aac aac ctg ctg acc aag ttc ctg agc acc ggt atg    720
Asp Tyr Asn His Asn Asn Leu Leu Thr Lys Phe Leu Ser Thr Gly Met
225                 230                 235                 240 gtc ttc gaa aac ctg gcc aag acc gtc ctg agc aac ctg ctg gat ggg    768
Val Phe Glu Asn Leu Ala Lys Thr Val Leu Ser Asn Leu Leu Asp Gly
                245                 250                 255 aac ctg cag ggg atg ctg aac atc agc cag cac cag tgt gtg aag aag    816
Asn Leu Gln Gly Met Leu Asn Ile Ser Gln His Gln Cys Val Lys Lys
            260                 265                 270 cag tgt ccc cag aac agc ggg tgt ttc aga cac ctg gat gag aga gag    864
Gln Cys Pro Gln Asn Ser Gly Cys Phe Arg His Leu Asp Glu Arg Glu
            275                 280                 285 gag tgt aag tgt ctg ctg aac tac aag cag gaa ggt gat aag tgt gtg    912
Glu Cys Lys Cys Leu Leu Asn Tyr Lys Gln Glu Gly Asp Lys Cys Val
        290                 295                 300 gaa aac ccc aat cct act tgt aac gag aac aat ggt gga tgt gat gcc    960
Glu Asn Pro Asn Pro Thr Cys Asn Glu Asn Asn Gly Gly Cys Asp Ala
305                 310                 315                 320 gat gcc aag tgt acc gag gag gat tca ggg agc aac ggg aag aag atc    1008
Asp Ala Lys Cys Thr Glu Glu Asp Ser Gly Ser Asn Gly Lys Lys Ile
                325                 330                 335 acc tgt gag tgt acc aag cct gat tct tat cca ctg ttc gat ggt atc    1056
Thr Cys Glu Cys Thr Lys Pro Asp Ser Tyr Pro Leu Phe Asp Gly Ile
            340                 345                 350 ttc tgt agt                                                        1065
Phe Cys Ser
        355

<210> SEQ ID NO 2
<211> LENGTH: 1088
<212> TYPE: DNA
<213> ORGANISM: Plasmodium falciparum
<220> FEATURE:
<221> NAME/KEY: CDS
<222> LOCATION: (1)...(1083)

<400> SEQUENCE: 2 gca gta act cct tcc gta att gat aac ata ctt tct aaa att gaa aat    48
Ala Val Thr Pro Ser Val Ile Asp Asn Ile Leu Ser Lys Ile Glu Asn
1               5                   10                  15 gaa tat gag gtt tta tat tta aaa cct tta gca ggt gtt tat aga agt    96
Glu Tyr Glu Val Leu Tyr Leu Lys Pro Leu Ala Gly Val Tyr Arg Ser
            20                  25                  30 tta aaa aaa caa tta gaa aat aac gtt atg aca ttt aat gtt aat gtt    144
Leu Lys Lys Gln Leu Glu Asn Asn Val Met Thr Phe Asn Val Asn Val
        35                  40                  45 aag gat att tta aat tca cga ttt aat aaa cgt gaa aat ttc aaa aat    192
Lys Asp Ile Leu Asn Ser Arg Phe Asn Lys Arg Glu Asn Phe Lys Asn
    50                  55                  60 gtt tta gaa tca gat tta att cca tat aaa gat tta aca tca agt aat    240
```

```
Val Leu Glu Ser Asp Leu Ile Pro Tyr Lys Asp Leu Thr Ser Ser Asn
 65                  70                  75                  80 tat gtt gtc aaa gat cca tat aaa ttt ctt aat aaa gaa aaa aga gat    288
Tyr Val Val Lys Asp Pro Tyr Lys Phe Leu Asn Lys Glu Lys Arg Asp
                 85                  90                  95 aaa ttc tta agc agt tat aat tat att aag gat tca ata gat acg gat    336
Lys Phe Leu Ser Ser Tyr Asn Tyr Ile Lys Asp Ser Ile Asp Thr Asp
                100                 105                 110 ata aat ttt gca aat gat gtt ctt gga tat tat aaa ata tta tcc gaa    384
Ile Asn Phe Ala Asn Asp Val Leu Gly Tyr Tyr Lys Ile Leu Ser Glu
            115                 120                 125 aaa tat aaa tca gat tta gat tca att aaa aaa tat atc aac gac aaa    432
Lys Tyr Lys Ser Asp Leu Asp Ser Ile Lys Lys Tyr Ile Asn Asp Lys
        130                 135                 140 caa ggt gaa aat gag aaa tac ctt ccc ttt tta aac aat att gag acc    480
Gln Gly Glu Asn Glu Lys Tyr Leu Pro Phe Leu Asn Asn Ile Glu Thr
145                 150                 155                 160 tta tat aaa aca gtt aat gat aaa att gat tta ttt gta att cat tta    528
Leu Tyr Lys Thr Val Asn Asp Lys Ile Asp Leu Phe Val Ile His Leu
                165                 170                 175 gaa gca aaa gtt cta aat tat aca tat gag aaa tca aac gta gaa gtt    576
Glu Ala Lys Val Leu Asn Tyr Thr Tyr Glu Lys Ser Asn Val Glu Val
                180                 185                 190 aaa ata aaa gaa ctt aat tac tta aaa aca att caa gac aaa ttg gca    624
Lys Ile Lys Glu Leu Asn Tyr Leu Lys Thr Ile Gln Asp Lys Leu Ala
            195                 200                 205 gat ttt aaa aaa aat aac aat ttc gtt gga att gct gat tta tca aca    672
Asp Phe Lys Lys Asn Asn Asn Phe Val Gly Ile Ala Asp Leu Ser Thr
210                 215                 220 gat tat aac cat aat aac tta ttg aca aag ttc ctt agt aca ggt atg    720
Asp Tyr Asn His Asn Asn Leu Leu Thr Lys Phe Leu Ser Thr Gly Met
225                 230                 235                 240 gtt ttt gaa aat ctt gct aaa acc gtt tta tct aat tta ctt gat gga    768
Val Phe Glu Asn Leu Ala Lys Thr Val Leu Ser Asn Leu Leu Asp Gly
                245                 250                 255 aac ttg caa ggt atg tta aac att tca caa cac caa tgc gta aaa aaa    816
Asn Leu Gln Gly Met Leu Asn Ile Ser Gln His Gln Cys Val Lys Lys
            260                 265                 270 caa tgt cca caa aat tct gga tgt ttc aga cat tta gat gaa aga gaa    864
Gln Cys Pro Gln Asn Ser Gly Cys Phe Arg His Leu Asp Glu Arg Glu
        275                 280                 285 gaa tgt aaa tgt tta tta aat tac aaa caa gaa ggt gat aaa tgt gtt    912
Glu Cys Lys Cys Leu Leu Asn Tyr Lys Gln Glu Gly Asp Lys Cys Val
    290                 295                 300 gaa aat cca aat cct act tgt aac gaa aat aat ggt gga tgt gat gca    960
Glu Asn Pro Asn Pro Thr Cys Asn Glu Asn Asn Gly Gly Cys Asp Ala
305                 310                 315                 320 gat gcc aaa tgt acc gaa gaa gat tca ggt agc aac gga aag aaa atc   1008
Asp Ala Lys Cys Thr Glu Glu Asp Ser Gly Ser Asn Gly Lys Lys Ile
                325                 330                 335 aca tgt gaa tgt act aaa cct gat tct tat cca ctt ttc gat ggt att   1056
Thr Cys Glu Cys Thr Lys Pro Asp Ser Tyr Pro Leu Phe Asp Gly Ile
            340                 345                 350 ttc tgc agt cac cac cac cac cac cac taact                         1088
Phe Cys Ser His His His His His His
        355                 360

<210> SEQ ID NO 3
<211> LENGTH: 88
<212> TYPE: DNA
```

-continued

<213> ORGANISM: Artificial Sequence
<220> FEATURE:
<223> OTHER INFORMATION: synthetically generated oligonucleotide

<400> SEQUENCE: 3
tcgacgagag ccatgaaggt cctcatcctt gcctgtctgg tggctctggc cattgcaaga     60
gagcaggaag aactcaatgt agtcggta                                         88

<210> SEQ ID NO 4
<211> LENGTH: 88
<212> TYPE: DNA
<213> ORGANISM: Artificial Sequence
<220> FEATURE:
<223> OTHER INFORMATION: synthetically generated oligonucleotide

<400> SEQUENCE: 4
gatctaccga ctacattgag ttcttcctgc tctcttgcaa tggccagagc caccagacag     60
gcaaggatga ggaccttcat ggctctcg                                         88

<210> SEQ ID NO 5
<211> LENGTH: 60
<212> TYPE: DNA
<213> ORGANISM: Artificial Sequence
<220> FEATURE:
<223> OTHER INFORMATION: oligonucleotide for PCR

<400> SEQUENCE: 5
taactcgagc gaaccatgaa ggtcctcatc cttgcctgtc tggtggctct ggccattgca     60

<210> SEQ ID NO 6
<211> LENGTH: 48
<212> TYPE: DNA
<213> ORGANISM: Artificial Sequence
<220> FEATURE:
<223> OTHER INFORMATION: oligonucleotide for PCR

<400> SEQUENCE: 6
aattctcgag ttagtggtgg tggtggtggt gactgcagaa ataccatc                   48

<210> SEQ ID NO 7
<211> LENGTH: 31
<212> TYPE: DNA
<213> ORGANISM: Artificial Sequence
<220> FEATURE:
<223> OTHER INFORMATION: oligonucleotide for PCR

<400> SEQUENCE: 7
aatagatctg cagtaactcc ttccgtaatt g                                     31

<210> SEQ ID NO 8
<211> LENGTH: 1142
<212> TYPE: DNA
<213> ORGANISM: Artificial Sequence
<220> FEATURE:
<223> OTHER INFORMATION: altered MSP sequence; preferably, a bacterium,
      virus, or parasite
<221> NAME/KEY: CDS
<222> LOCATION: (1)...(1142)

<400> SEQUENCE: 8 atg aag gtc ctc ata att gcc tgt ctg gtg gct ctg gcc att gca gcc     48
Met Lys Val Leu Ile Ile Ala Cys Leu Val Ala Leu Ala Ile Ala Ala
 1               5                  10                  15 gtc act ccc tcc gtc atc gat aac atc ctg tcc aag atc gag aac gag     96
Val Thr Pro Ser Val Ile Asp Asn Ile Leu Ser Lys Ile Glu Asn Glu -continued

```
                    20                      25                      30
tac gag gtg ctg tac ctg aag ccc ctg gca gga gtc tac agg agc ctg      144
Tyr Glu Val Leu Tyr Leu Lys Pro Leu Ala Gly Val Tyr Arg Ser Leu
             35                      40                      45 aag aag cag ctg gag aac aac gtg atg acc ttc aac gtg aac gtg aag      192
Lys Lys Gln Leu Glu Asn Asn Val Met Thr Phe Asn Val Asn Val Lys
     50                      55                      60 gat atc ctg aac agc agg ttc aac aag agg gag aac ttc aag aac gtg      240
Asp Ile Leu Asn Ser Arg Phe Asn Lys Arg Glu Asn Phe Lys Asn Val
 65                      70                      75                      80 ctg gag agc gat ctg atc ccc tac aag gat ctg acc agc agc aac tac      288
Leu Glu Ser Asp Leu Ile Pro Tyr Lys Asp Leu Thr Ser Ser Asn Tyr
                     85                      90                      95 gtg gtc aaa gat ccc tac aag ttc ctg aac aag gag aag aga gat aag      336
Val Val Lys Asp Pro Tyr Lys Phe Leu Asn Lys Glu Lys Arg Asp Lys
             100                     105                     110 ttc ctg agc agt tac aat tac atc aag gat agc att gac acc gat atc      384
Phe Leu Ser Ser Tyr Asn Tyr Ile Lys Asp Ser Ile Asp Thr Asp Ile
     115                     120                     125 aac ttc gcc aac gat gtc ctg gga tac tac aag atc ctg tcc gag aag      432
Asn Phe Ala Asn Asp Val Leu Gly Tyr Tyr Lys Ile Leu Ser Glu Lys
 130                     135                     140 tac aag agc gat ctg gat agc atc aag aag tac atc aac gat aag cag      480
Tyr Lys Ser Asp Leu Asp Ser Ile Lys Lys Tyr Ile Asn Asp Lys Gln
145                     150                     155                     160 gga gag aac gag aag tac ctg ccc ttc ctg aac aac atc gag acc ctg      528
Gly Glu Asn Glu Lys Tyr Leu Pro Phe Leu Asn Asn Ile Glu Thr Leu
                     165                     170                     175 tac aag acc gtc aac gat aag att gat ctg ttc gtg atc cac ctg gag      576
Tyr Lys Thr Val Asn Asp Lys Ile Asp Leu Phe Val Ile His Leu Glu
             180                     185                     190 gcc aag gtc ctg cag tac aca tat gag aag agc aac gtg gag gtc aag      624
Ala Lys Val Leu Gln Tyr Thr Tyr Glu Lys Ser Asn Val Glu Val Lys
     195                     200                     205 atc aag gag ctg aat tac ctg aag acc atc cag gat aag ctg gcc gat      672
Ile Lys Glu Leu Asn Tyr Leu Lys Thr Ile Gln Asp Lys Leu Ala Asp
 210                     215                     220 ttc aag aag aac aac aac ttc gtc gga atc gcc gat ctg agc acc gat      720
Phe Lys Lys Asn Asn Asn Phe Val Gly Ile Ala Asp Leu Ser Thr Asp
225                     230                     235                     240 tac aac cac aac aac ctg ctg acc aag ttc ctg agc acc gga atg gtc      768
Tyr Asn His Asn Asn Leu Leu Thr Lys Phe Leu Ser Thr Gly Met Val
                     245                     250                     255 ttc gaa aac ctg gcc aag acc gtc ctg agc aac ctg ctg gat gga aac      816
Phe Glu Asn Leu Ala Lys Thr Val Leu Ser Asn Leu Leu Asp Gly Asn
             260                     265                     270 ctg cag gga atg ctg cag atc agc cag cac cag tgt gtg aag aag cag      864
Leu Gln Gly Met Leu Gln Ile Ser Gln His Gln Cys Val Lys Lys Gln
     275                     280                     285 tgt ccc cag aac agc gga tgc ttc aga cac ctg gat gag agg gag gag      912
Cys Pro Gln Asn Ser Gly Cys Phe Arg His Leu Asp Glu Arg Glu Glu
 290                     295                     300 tgc aag tgc ctg ctg aac tac aag cag gaa gga gat aag tgt gtg gaa      960
Cys Lys Cys Leu Leu Asn Tyr Lys Gln Glu Gly Asp Lys Cys Val Glu
305                     310                     315                     320 aac ccc aat cct act tgt aac gag aac aat gga gga tgc gat gcc gat     1008
Asn Pro Asn Pro Thr Cys Asn Glu Asn Asn Gly Gly Cys Asp Ala Asp
                     325                     330                     335 gcc aag tgt acc gag gag gat tca gga agc aac gga aag aag atc acc     1056
```

```
Ala Lys Cys Thr Glu Glu Asp Ser Gly Ser Asn Gly Lys Lys Ile Thr
            340                 345                 350 tgc gag tgt acc aag cct gat tct tat cca ctg ttc gat ggt att ttc    1104
Cys Glu Cys Thr Lys Pro Asp Ser Tyr Pro Leu Phe Asp Gly Ile Phe
            355                 360                 365 tgc agt cac cac cac cac cac taa ctc gag gat cc                      1142
Cys Ser His His His His His His  *  Leu Glu Asp
            370                 375
```

<210> SEQ ID NO 9
<211> LENGTH: 355
<212> TYPE: PRT
<213> ORGANISM: Artificial Sequence
<220> FEATURE:
<223> OTHER INFORMATION: altered MSP sequence; preferably, a bacterium,
      virus, or parasite

<400> SEQUENCE: 9

```
Ala Val Thr Pro Ser Val Ile Asp Asn Ile Leu Ser Lys Ile Glu Asn
 1               5                  10                  15

Glu Tyr Glu Val Leu Tyr Leu Lys Pro Leu Ala Gly Val Tyr Arg Ser
            20                  25                  30

Leu Lys Lys Gln Leu Glu Asn Asn Val Met Thr Phe Asn Val Asn Val
        35                  40                  45

Lys Asp Ile Leu Asn Ser Arg Phe Asn Lys Arg Glu Asn Phe Lys Asn
 50                  55                  60

Val Leu Glu Ser Asp Leu Ile Pro Tyr Lys Asp Leu Thr Ser Ser Asn
65                  70                  75                  80

Tyr Val Val Lys Asp Pro Tyr Lys Phe Leu Asn Lys Glu Lys Arg Asp
                85                  90                  95

Lys Phe Leu Ser Ser Tyr Asn Tyr Ile Lys Asp Ser Ile Asp Thr Asp
            100                 105                 110

Ile Asn Phe Ala Asn Asp Val Leu Gly Tyr Tyr Lys Ile Leu Ser Glu
        115                 120                 125

Lys Tyr Lys Ser Asp Leu Asp Ser Ile Lys Lys Tyr Ile Asn Asp Lys
130                 135                 140

Gln Gly Glu Asn Glu Lys Tyr Leu Pro Phe Leu Asn Asn Ile Glu Thr
145                 150                 155                 160

Leu Tyr Lys Thr Val Asn Asp Lys Ile Asp Leu Phe Val Ile His Leu
                165                 170                 175

Glu Ala Lys Val Leu Asn Tyr Thr Tyr Glu Lys Ser Asn Val Glu Val
            180                 185                 190

Lys Ile Lys Glu Leu Asn Tyr Leu Lys Thr Ile Gln Asp Lys Leu Ala
        195                 200                 205

Asp Phe Lys Lys Asn Asn Asn Phe Val Gly Ile Ala Asp Leu Ser Thr
210                 215                 220

Asp Tyr Asn His Asn Asn Leu Leu Thr Lys Phe Leu Ser Thr Gly Met
225                 230                 235                 240

Val Phe Glu Asn Leu Ala Lys Thr Val Leu Ser Asn Leu Leu Asp Gly
                245                 250                 255

Asn Leu Gln Gly Met Leu Asn Ile Ser Gln His Gln Cys Val Lys Lys
            260                 265                 270

Gln Cys Pro Gln Asn Ser Gly Cys Phe Arg His Leu Asp Glu Arg Glu
        275                 280                 285

Glu Cys Lys Cys Leu Leu Asn Tyr Lys Gln Glu Gly Asp Lys Cys Val
290                 295                 300
```

```
Glu Asn Pro Asn Pro Thr Cys Asn Glu Asn Asn Gly Gly Cys Asp Ala
305                 310                 315                 320

Asp Ala Lys Cys Thr Glu Glu Asp Ser Gly Ser Asn Gly Lys Lys Ile
            325                 330                 335

Thr Cys Glu Cys Thr Lys Pro Asp Ser Tyr Pro Leu Phe Asp Gly Ile
                340                 345                 350

Phe Cys Ser
        355

<210> SEQ ID NO 10
<211> LENGTH: 361
<212> TYPE: PRT
<213> ORGANISM: Plasmodium falciparum

<400> SEQUENCE: 10

Ala Val Thr Pro Ser Val Ile Asp Asn Ile Leu Ser Lys Ile Glu Asn
1               5                   10                  15

Glu Tyr Glu Val Leu Tyr Leu Lys Pro Leu Ala Gly Val Tyr Arg Ser
                20                  25                  30

Leu Lys Lys Gln Leu Glu Asn Asn Val Met Thr Phe Asn Val Asn Val
            35                  40                  45

Lys Asp Ile Leu Asn Ser Arg Phe Asn Lys Arg Glu Asn Phe Lys Asn
    50                  55                  60

Val Leu Glu Ser Asp Leu Ile Pro Tyr Lys Asp Leu Thr Ser Ser Asn
65                  70                  75                  80

Tyr Val Val Lys Asp Pro Tyr Lys Phe Leu Asn Lys Glu Lys Arg Asp
                85                  90                  95

Lys Phe Leu Ser Ser Tyr Asn Tyr Ile Lys Asp Ser Ile Asp Thr Asp
            100                 105                 110

Ile Asn Phe Ala Asn Asp Val Leu Gly Tyr Tyr Lys Ile Leu Ser Glu
        115                 120                 125

Lys Tyr Lys Ser Asp Leu Asp Ser Ile Lys Lys Tyr Ile Asn Asp Lys
    130                 135                 140

Gln Gly Glu Asn Glu Lys Tyr Leu Pro Phe Leu Asn Asn Ile Glu Thr
145                 150                 155                 160

Leu Tyr Lys Thr Val Asn Asp Lys Ile Asp Leu Phe Val Ile His Leu
                165                 170                 175

Glu Ala Lys Val Leu Asn Tyr Thr Tyr Glu Lys Ser Asn Val Glu Val
            180                 185                 190

Lys Ile Lys Glu Leu Asn Tyr Leu Lys Thr Ile Gln Asp Lys Leu Ala
        195                 200                 205

Asp Phe Lys Lys Asn Asn Phe Val Gly Ile Ala Asp Leu Ser Thr
    210                 215                 220

Asp Tyr Asn His Asn Asn Leu Leu Thr Lys Phe Leu Ser Thr Gly Met
225                 230                 235                 240

Val Phe Glu Asn Leu Ala Lys Thr Val Leu Ser Asn Leu Leu Asp Gly
                245                 250                 255

Asn Leu Gln Gly Met Leu Asn Ile Ser Gln His Gln Cys Val Lys Lys
            260                 265                 270

Gln Cys Pro Gln Asn Ser Gly Cys Phe Arg His Leu Asp Glu Arg Glu
        275                 280                 285

Glu Cys Lys Cys Leu Leu Asn Tyr Lys Gln Glu Gly Asp Lys Cys Val
    290                 295                 300

Glu Asn Pro Asn Pro Thr Cys Asn Glu Asn Asn Gly Gly Cys Asp Ala
305                 310                 315                 320
```

```
Asp Ala Lys Cys Thr Glu Glu Asp Ser Gly Ser Asn Gly Lys Lys Ile
            325                 330                 335

Thr Cys Glu Cys Thr Lys Pro Asp Ser Tyr Pro Leu Phe Asp Gly Ile
            340                 345                 350

Phe Cys Ser His His His His His His
            355                 360

<210> SEQ ID NO 11
<211> LENGTH: 379
<212> TYPE: PRT
<213> ORGANISM: Artificial Sequence
<220> FEATURE:
<223> OTHER INFORMATION: altered MSP sequence; preferably, a bacterium,
      virus, or parasite

<400> SEQUENCE: 11

Met Lys Val Leu Ile Ile Ala Cys Leu Val Ala Leu Ala Ile Ala Ala
  1               5                  10                  15

Val Thr Pro Ser Val Ile Asp Asn Ile Leu Ser Lys Ile Glu Asn Glu
             20                  25                  30

Tyr Glu Val Leu Tyr Leu Lys Pro Leu Ala Gly Val Tyr Arg Ser Leu
         35                  40                  45

Lys Lys Gln Leu Glu Asn Asn Val Met Thr Phe Asn Val Asn Val Lys
     50                  55                  60

Asp Ile Leu Asn Ser Arg Phe Asn Lys Arg Glu Asn Phe Lys Asn Val
 65                  70                  75                  80

Leu Glu Ser Asp Leu Ile Pro Tyr Lys Asp Leu Thr Ser Ser Asn Tyr
                 85                  90                  95

Val Val Lys Asp Pro Tyr Lys Phe Leu Asn Lys Glu Lys Arg Asp Lys
            100                 105                 110

Phe Leu Ser Ser Tyr Asn Tyr Ile Lys Asp Ser Ile Asp Thr Asp Ile
        115                 120                 125

Asn Phe Ala Asn Asp Val Leu Gly Tyr Tyr Lys Ile Leu Ser Glu Lys
130                 135                 140

Tyr Lys Ser Asp Leu Asp Ser Ile Lys Lys Tyr Ile Asn Asp Lys Gln
145                 150                 155                 160

Gly Glu Asn Glu Lys Tyr Leu Pro Phe Leu Asn Asn Ile Glu Thr Leu
                165                 170                 175

Tyr Lys Thr Val Asn Asp Lys Ile Asp Leu Phe Val Ile His Leu Glu
            180                 185                 190

Ala Lys Val Leu Gln Tyr Thr Tyr Glu Lys Ser Asn Val Glu Val Lys
        195                 200                 205

Ile Lys Glu Leu Asn Tyr Leu Lys Thr Ile Gln Asp Lys Leu Ala Asp
    210                 215                 220

Phe Lys Lys Asn Asn Asn Phe Val Gly Ile Ala Asp Leu Ser Thr Asp
225                 230                 235                 240

Tyr Asn His Asn Asn Leu Leu Thr Lys Phe Leu Ser Thr Gly Met Val
                245                 250                 255

Phe Glu Asn Leu Ala Lys Thr Val Leu Ser Asn Leu Leu Asp Gly Asn
            260                 265                 270

Leu Gln Gly Met Leu Gln Ile Ser Gln His Gln Cys Val Lys Lys Gln
        275                 280                 285

Cys Pro Gln Asn Ser Gly Cys Phe Arg His Leu Asp Glu Arg Glu Glu
    290                 295                 300

Cys Lys Cys Leu Leu Asn Tyr Lys Gln Glu Gly Asp Lys Cys Val Glu
```

```
                305                 310                 315                 320
Asn Pro Asn Pro Thr Cys Asn Glu Asn Asn Gly Gly Cys Asp Ala Asp
                    325                 330                 335

Ala Lys Cys Thr Glu Glu Asp Ser Gly Ser Asn Gly Lys Lys Ile Thr
                340                 345                 350

Cys Glu Cys Thr Lys Pro Asp Ser Tyr Pro Leu Phe Asp Gly Ile Phe
            355                 360                 365

Cys Ser His His His His His His Leu Glu Asp
        370                 375
```

```
<210> SEQ ID NO 12
<211> LENGTH: 82
<212> TYPE: DNA
<213> ORGANISM: Artificial Sequence
<220> FEATURE:
<223> OTHER INFORMATION: synthetically generated oligonucleotide

<400> SEQUENCE: 12
ggccgctcga cgccaccatg aaggtcctca taattgcctg tctggtggct ctggccattg    60
cagccgtcac tccctccgtc at                                             82

<210> SEQ ID NO 13
<211> LENGTH: 80
<212> TYPE: DNA
<213> ORGANISM: Artificial Sequence
<220> FEATURE:
<223> OTHER INFORMATION: synthetically generated oligonucleotide

<400> SEQUENCE: 13
cgatgacgga gggagtgacg gctgcaatgg ccagagccac cagacaggca attatgagga    60
ccttcatggt ggcgtcgagc                                                80

<210> SEQ ID NO 14
<211> LENGTH: 27
<212> TYPE: DNA
<213> ORGANISM: Artificial Sequence
<220> FEATURE:
<223> OTHER INFORMATION: oligonucleotide for PCR

<400> SEQUENCE: 14
gattgacaag taatacgctg tttcctc                                        27

<210> SEQ ID NO 15
<211> LENGTH: 17
<212> TYPE: DNA
<213> ORGANISM: Artificial Sequence
<220> FEATURE:
<223> OTHER INFORMATION: oligonucleotide for PCR

<400> SEQUENCE: 15
ggattcaata gatacgg                                                   17

<210> SEQ ID NO 16
<211> LENGTH: 21
<212> TYPE: DNA
<213> ORGANISM: Artificial Sequence
<220> FEATURE:
<223> OTHER INFORMATION: oligonucleotide for PCR

<400> SEQUENCE: 16
cagggaatgc tgcagatcag c                                              21
```

-continued

```
<210> SEQ ID NO 17
<211> LENGTH: 49
<212> TYPE: DNA
<213> ORGANISM: Artificial Sequence
<220> FEATURE:
<223> OTHER INFORMATION: oligonucleotide for PCR

<400> SEQUENCE: 17
aattctcgag ttagtggtgg tggtggtggt gatcgcagaa aataccatg          49

<210> SEQ ID NO 18
<211> LENGTH: 24
<212> TYPE: DNA
<213> ORGANISM: Artificial Sequence
<220> FEATURE:
<223> OTHER INFORMATION: oligonucleotide for PCR

<400> SEQUENCE: 18
ctccttgttc aggaacttgt aggg                                     24

<210> SEQ ID NO 19
<211> LENGTH: 21
<212> TYPE: DNA
<213> ORGANISM: Artificial Sequence
<220> FEATURE:
<223> OTHER INFORMATION: oligonucleotide for PCR

<400> SEQUENCE: 19
gtcctgcagt acacatatga g                                        21
```